(12) United States Patent
Clark et al.

(10) Patent No.: US 7,082,843 B2
(45) Date of Patent: Aug. 1, 2006

(54) FLUID FLOW MEASUREMENT DEVICE

(75) Inventors: Gene E. Clark, Redwood, CA (US);
Steve T. Cho, Sunnyvale, CA (US);
Harlow B. Christianson, San Jose, CA (US); John M. Sperinde, Saratoga, CA (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 11/205,929

(22) Filed: Aug. 17, 2005

(65) Prior Publication Data

US 2006/0010989 A1    Jan. 19, 2006

Related U.S. Application Data

(63) Continuation of application No. 10/978,866, filed on Oct. 29, 2004, now Pat. No. 6,964,204, which is a continuation of application No. 10/442,575, filed on May 21, 2003, now Pat. No. 6,813,964.

(51) Int. Cl.
*G01F 1/22* (2006.01)

(52) U.S. Cl. .................................. 73/861.53

(58) Field of Classification Search ............. 73/861.42, 73/861.52, 861.53, 861.58, 861.61, 861.62
See application file for complete search history.

(56) References Cited

U.S. PATENT DOCUMENTS

| | | | |
|---|---|---|---|
| 4,278,085 A | 7/1981 | Shim | |
| 4,443,218 A | 4/1984 | DeCant et al. | |
| 4,447,224 A | 5/1984 | DeCant et al. | |
| 4,925,444 A | 5/1990 | Orkin | |
| 5,287,851 A | 2/1994 | Beran et al. | |
| 5,342,298 A | 8/1994 | Michaels | |
| 5,429,601 A | 7/1995 | Conley | |
| 6,110,152 A | 8/2000 | Kovelman | |
| 6,280,408 B1 | 8/2001 | Sipin | |
| 6,349,740 B1 | 2/2002 | Cho et al. | |
| 6,413,238 B1 | 7/2002 | Maget | |
| 6,445,053 B1 | 9/2002 | Cho | |
| 6,564,825 B1 * | 5/2003 | Lowery et al. | 137/487.5 |
| 6,685,668 B1 | 2/2004 | Cho et al. | |

* cited by examiner

*Primary Examiner*—Harshad Patel
(74) *Attorney, Agent, or Firm*—Michael R. Crabb

(57) ABSTRACT

The invention is directed to a device for obtaining flow rate measurements including a sensor assembly and a housing. The sensor assembly includes a body defining a first fluid flow passage having an inlet, an outlet, a flow restricting element in the first fluid flow passage between the inlet and the outlet, an upstream fluid pressure sensor, a downstream fluid pressure sensor, an upstream signal contact connected to the upstream fluid pressure sensor, and a downstream signal contact connected to the downstream fluid pressure sensor. The housing has an upstream portion defining an upstream port, a downstream portion defining a downstream port, and a probe access port configured to provide access of a probe to at least one of the upstream signal contact and downstream signal contact. The housing can also define a second fluid flow passage in parallel with the first fluid flow passage. The device can be disposable.

3 Claims, 19 Drawing Sheets

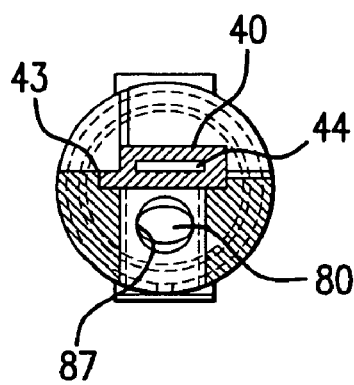
FIG.8(d)
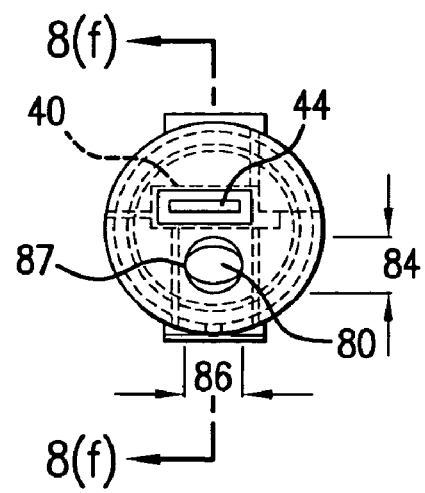
FIG.8(e)
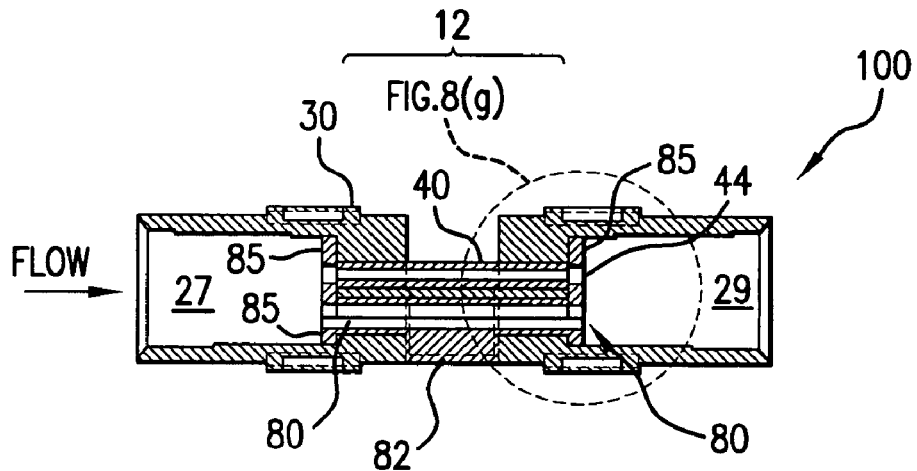
FIG.8(f)
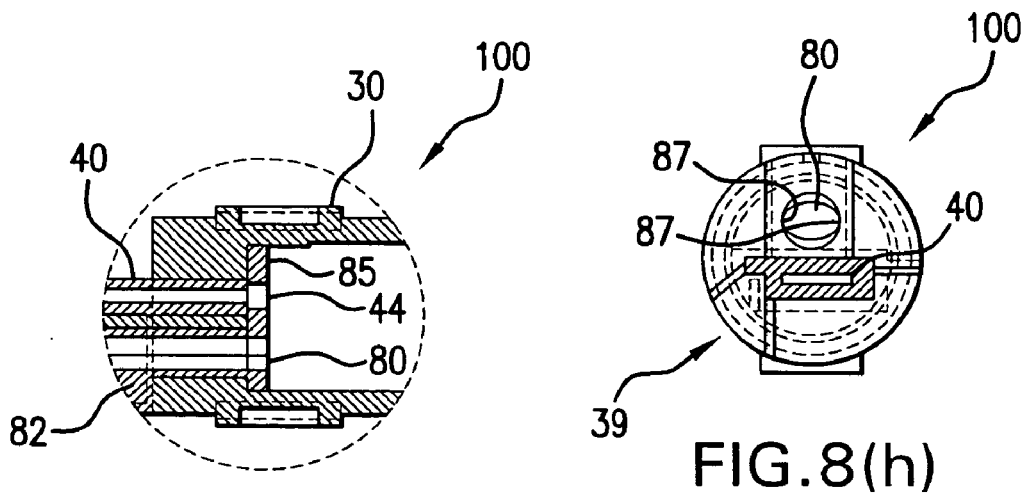
FIG.8(g)
FIG.8(h)

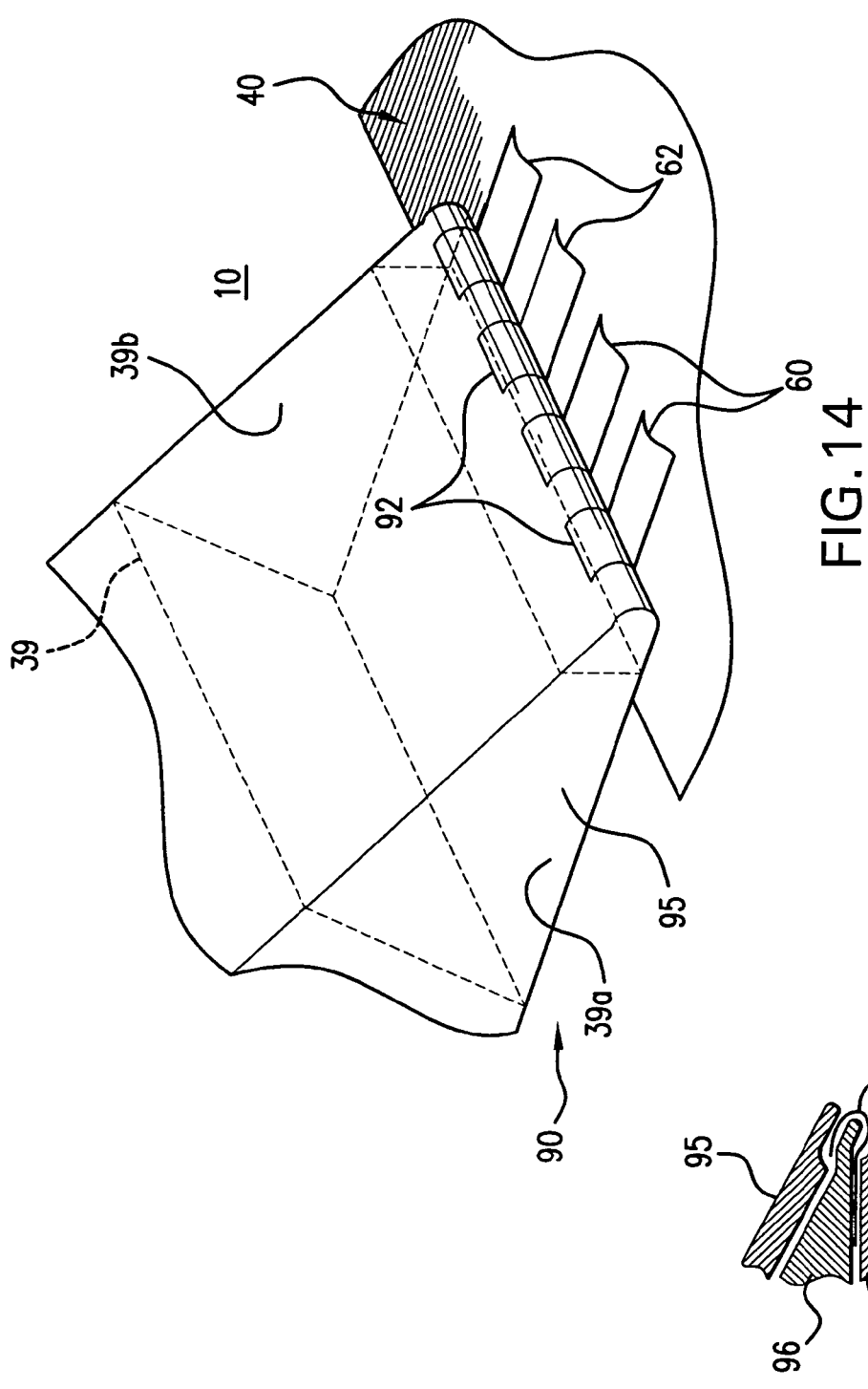

FLUID FLOW MEASUREMENT DEVICE

CROSS REFERENCE TO RELATED APPLICATION

This application is a continuation of U.S. Ser. No. 10/978,866 filed on Oct. 29, 2004, now allowed, which is a continuation of Ser. No. 10/442,575 filed on May 21, 2003, now U.S. Pat. No. 6,813,964

BACKGROUND OF THE INVENTION

1. Field of the Invention

The present invention relates to a flow sensor device to obtain flow characteristics of a fluid flow system, such as a system used in administering a beneficial agent to a patient. Particularly, the present invention is directed to a flow measurement device including first and second pressure sensors in a flow passage to measure a flow of beneficial agent and, optionally, the presence of air in the fluid flow system. The invention also includes a related system and method for obtaining such flow characteristics.

2. Description of Related Art

When administering a predetermined amount of a beneficial agent to a patient over an extended period of time in liquid form, it is beneficial, if not necessary, to obtain and monitor relevant flow characteristics such as flow rates and the presence of air. While methods for obtaining such information have existed for a long time, to date, no reliable low cost systems have been developed for disposable use.

For example, fluid flow measurements within a disposable IV fluid line or similar feed set generally have not been financially and technically viable up to this point in time. Low cost electronic flow sensors have existed for some time, but have to date not presented a viable alternative for solving this problem. Limitations to commercialization of such a device have included inadequate dynamic range of low-cost flow sensor systems and the unacceptable costs of total sensor assembly.

One problem with making flow sensors low cost is in the manufacturing process. Silicon chips typically are wire-bonded to a lead frame that is encapsulated and soldered to a printed circuit board. This configuration requires the manual step of welding wires from the chip to the lead frame, which can result in significant additional manufacturing costs.

Likewise, there has been a long-felt need in the medical field for an economical and reliable system to detect the presence of air in IV lines or other medical feed sets. Typically, the presence of air in a fluid line has been sensed externally to the fluid path using a separate ultrasound or optical sensor that must communicate through the disposable tubing or molded component of the fluid path. The ultrasound approach may be subject to misalignment and other geometry changes that can impact the signal conduction around and through the fluid inside the tubing or other components of the disposable fluid path. The optical approach requires specific molded geometries within the fluid path that are reflective or conductive depending on the presence of air or liquid. These systems are subject to variability in and interfacing to the disposable fluid path. Also, the added cost of this air detection system is an impediment to its widespread adoption.

Thus, there remains a need in the art for a reliable fluid flow detection system that is sufficiently inexpensive to allow use in disposable applications. There is also a continued need for an inexpensive and reliable system to detect the presence of air in fluid systems, such as IV lines and feed sets.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention is directed to a device for obtaining flow characteristics of a fluid flow system.

The device includes a sensor assembly. The sensor assembly includes a body defining a first fluid flow passage having an inlet and an outlet, and a flow restricting element located along the first fluid flow passage between the inlet and the outlet. An upstream fluid pressure sensor is provided to sense an upstream fluid pressure at an upstream location in the first fluid flow passage between the inlet and the flow restricting element. The sensor assembly also includes a downstream fluid pressure sensor to sense a downstream fluid pressure at a downstream location in the first fluid flow passage between the flow restricting element and the outlet. The sensor assembly also includes an upstream signal contact connected to the upstream fluid pressure sensor, and a downstream signal contact connected to the downstream fluid pressure sensor.

The device also includes a housing. The housing has an upstream portion and a downstream portion. The upstream portion of the housing defines an upstream port in fluid communication with the inlet of the sensor assembly. The downstream portion of the housing defines a downstream port in fluid communication with the outlet of the sensor assembly. The housing also defines a probe access port configured to provide access of a probe to at least one of the upstream signal contact and downstream signal contact.

In accordance with another aspect of the invention, the housing has at least one registration surface configured to ensure proper registration of the device with a fluid flow system. The registration surface ensures the upstream port is aligned with a fluid source. The registration surface can include a surface configuration on the upstream portion of the housing that is different from a surface configuration on the downstream portion of the housing. In accordance with one aspect of the invention, the registration surface includes at least one planar surface. The registration surface can also include a detent.

In accordance with a further aspect of the invention, the housing defines a cavity of predetermined shape, and the sensor assembly has a corresponding shape so as to be received by the cavity. The cavity has at least one surface, and the surface can include at least one recess to receive a material to hold the sensor assembly within the cavity. A cap can further be positioned in the cavity proximate to the sensor assembly. The housing can have a connector, such as a Luer connector or a flange, proximate to at least one of the upstream port and the downstream port for connection with the fluid flow system.

In accordance with another aspect of the invention, the housing can define a second fluid flow passage therethrough. The second fluid flow passage can be arranged for fluid communication in parallel with the first fluid flow passage between the upstream port and the downstream port. A valve can further be provided for selective flow through the second fluid flow passage. For example, the valve can be formed as a compressible wall member defining at least a portion of the second fluid flow passage. The compressible wall member can be formed from an elastomeric material. In a preferred embodiment, the second fluid flow passage has a first transverse dimension and a second transverse dimension perpendicular to the first transverse dimension. Preferably, the first dimension is smaller than the second dimension so as to be more readily compressible. Preferably, the cross section of the second fluid flow passage has an ellipsoidal shape with a small radius at each apex of the ellipse to facilitate compression of the second fluid flow passage.

In accordance with another aspect of the invention, a fluid sensor system is provided. The system includes a device for obtaining flow rate measurements as described above, as well as a probe to receive signals representative of a fluid flow characteristic and a processor to process such signals. The probe can include a connector body having a predetermined shape, such as a wedge configuration, wherein the probe access port has a corresponding shape to ensure proper alignment of the probe with at least one of the upstream signal contact and downstream signal contact. The probe also includes a plurality of leads. At least one lead is provided for communication with the upstream signal contact and at least one lead is provided for communication with the downstream signal contact. At least one lead on the probe is configured to wipe across at least one of the upstream signal contact and the downstream signal contact. Preferably, the housing is configured to provide contact on one longitudinal surface and one vertical surface of the housing and provide for adequate force to ensure contact between the lead on the probe and the upstream signal contact and the downstream signal contact. The signal contacts can be in close proximity to registration surfaces on the outside of the housing that are engaged with an external clamp assembly that is also referenced to the probe.

In accordance with a further aspect of the invention, the system further includes a fluid flow line in communication with a fluid source. A locking mechanism preferably is provided to mate the housing with the fluid flow line. The locking mechanism has an unlocked condition for receipt of the housing, a first locked condition to align the housing with the fluid flow line and a second locked condition to position the probe in the housing. Additionally, if a second fluid flow passage with a valve is defined in the housing as described above, the system can further include an actuator to change the valve from the first condition to the second condition when the locking mechanism is moved from the first locked condition to the second locked condition. The actuator can include a protrusion to compress the elastic wall member. In one embodiment of the invention, the protrusion is a pin.

In further accordance with the invention, the fluid source includes a pump connected to the fluid flow system to selectively pump fluid through the first fluid flow passage. The processor is configured to control the pump in response to signals obtained by the probe from the sensors.

In further accordance with the invention a method of obtaining flow measurements is provided. The method includes providing a device for obtaining flow rate measurements as described above; directing a fluid flow through the first fluid flow passage; obtaining a signal corresponding to the fluid pressure in the first fluid flow passage at the locations of the upstream fluid pressure sensor and the downstream fluid pressure sensor; and determining a flow characteristic based upon the signal.

In accordance with a further aspect of the invention, the determining step includes determining the pressure difference between the upstream and downstream fluid pressure sensors. The determining step can further include calculating a flow rate of fluid through the first fluid flow passage based on the pressure difference.

In accordance with another aspect of the invention, the determining step includes detecting the presence of air in the first fluid flow passage. The step of detecting air in the first fluid flow passage can include identifying convergence and specific waveforms of the signal received from the upstream fluid pressure sensor and the signal received from the downstream fluid pressure sensor.

In accordance with yet another aspect of the invention, a method is provided further including the steps of intermittently pulsing the fluid through the first fluid flow passage and determining the amount of fluid delivered with each pulse by detecting the fluid pressure in the first fluid flow passage using the upstream fluid pressure sensor and the downstream fluid pressure sensor.

In accordance with still another aspect of the invention, a method is provided wherein the housing provided by the housing step includes a second fluid flow passage and a valve for selection of flow through the second fluid flow passage. The valve has a first condition to allow flow through the second flow passage and a second condition to prevent flow through the second flow passage. The method further includes the step of opening the valve to increase flow through the housing.

BRIEF DESCRIPTION OF THE DRAWINGS

FIGS. 8(a)–8(d) are a plan view and section views of the device of FIGS. 7(a)–7(e) after a second stage of a manufacturing process;

FIGS. 8(e)–8(h) are an end view and cross-sectional views of the device of FIGS. 7(a)–7(e) after a second stage of a manufacturing process.

FIGS. 14 and 14(a) are a perspective view and enlarged detail of a representative embodiment of a probe for use in accordance with the present invention.

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the apparatus. The methods and apparatus presented herein are used for obtaining flow characteristics of a fluid flow system, such as flow rate measurements or the like. The present invention is particularly suited for the controlled administration of beneficial agents to a patient, particularly in cases where a steady amount of beneficial agent is to be metered out over extended periods of time (e.g., days). In accordance with the invention, it is possible and desired to provide a device for obtaining such measurements that is inexpensive to manufacture and easy to use. The invention has a particular advantage for use in intravenous (IV) applications or similar feed sets, wherein the flow system including the reservoir and feed tube are intended to be disposable after use.

Figure 1A:
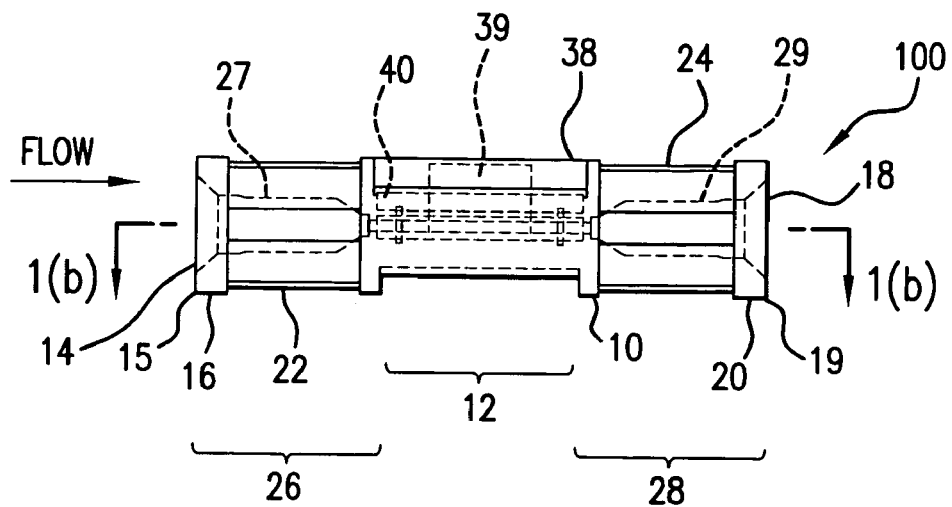
FIGS. 1(a)–1(c) are a side view and cross-sectional views, respectively, of a first representative embodiment of the device for obtaining flow characteristics in accordance with the present invention.
Figure 1B:
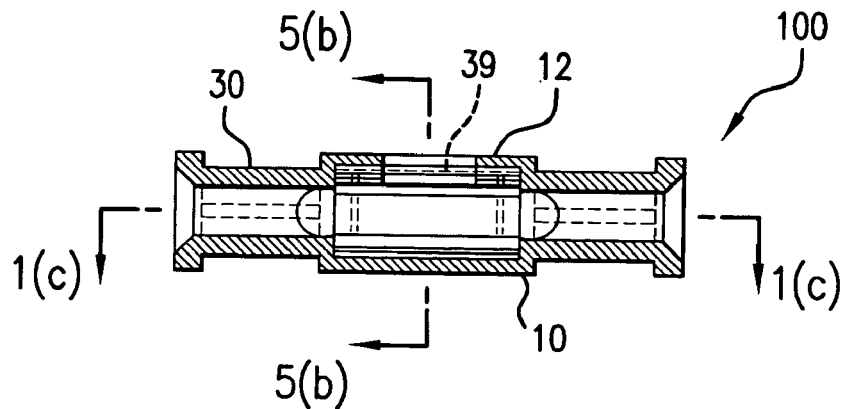
Figure 1C:
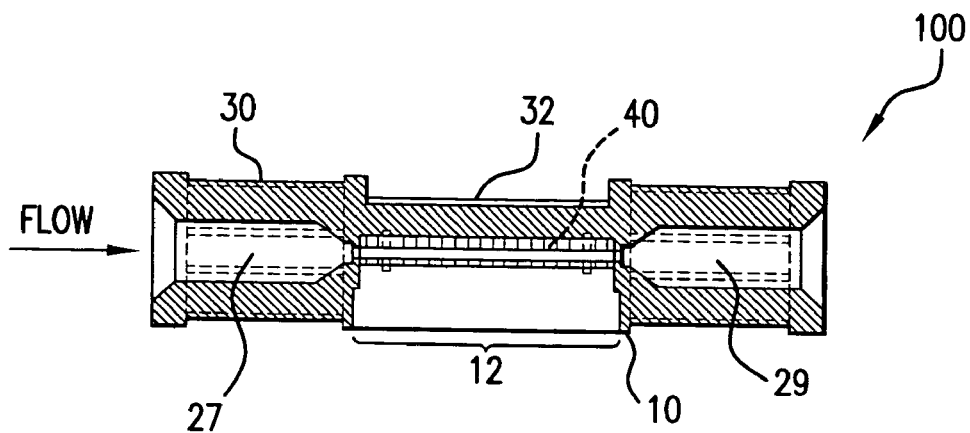

For purpose of explanation and illustration, and not limitation, an exemplary embodiment of the device for obtaining flow characteristics in accordance with the invention is shown in FIGS. 1(a)–1(c) and is designated generally by reference character 100. This exemplary embodiment is also depicted in FIGS. 2–6. Additional embodiments are shown in FIGS. 7–8 and 11–12 for purpose of illustration and not limitation.

Figure 2A:
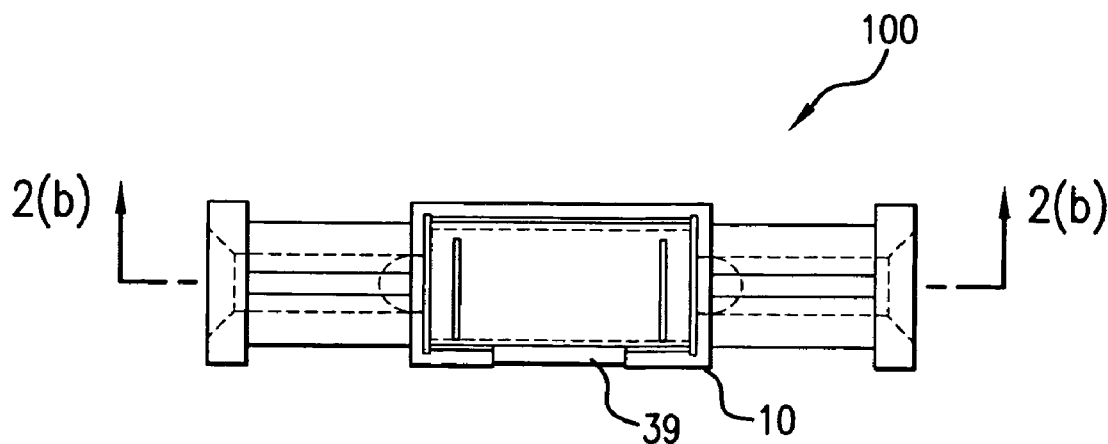
FIGS. 2(a)–2(c) are a plan view, a cross-sectional side view, and an end view, respectively, of the device of FIGS. 1(a)–1(c).
Figure 2B:
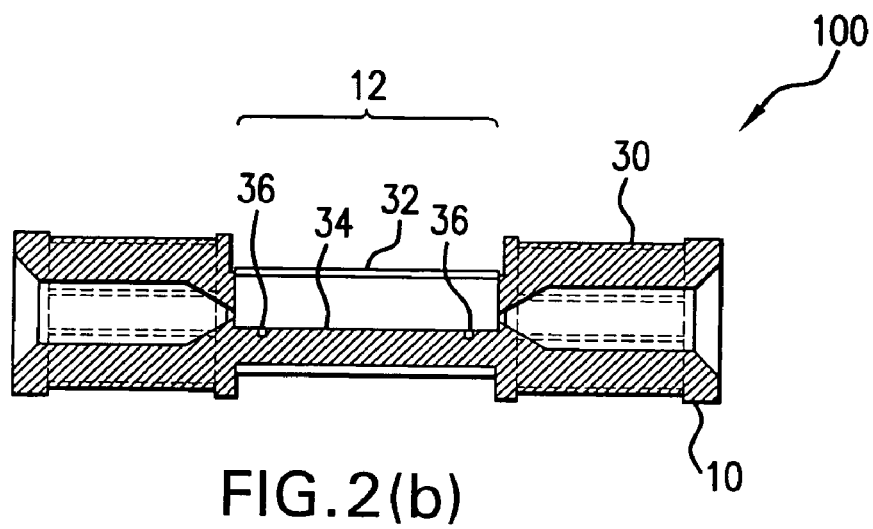
Figure 2C:
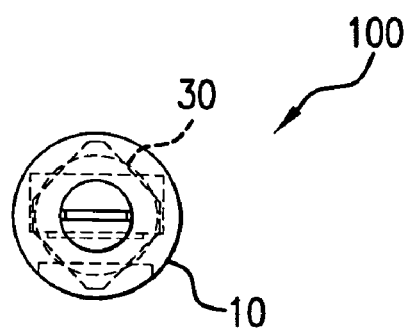
Figure 3:
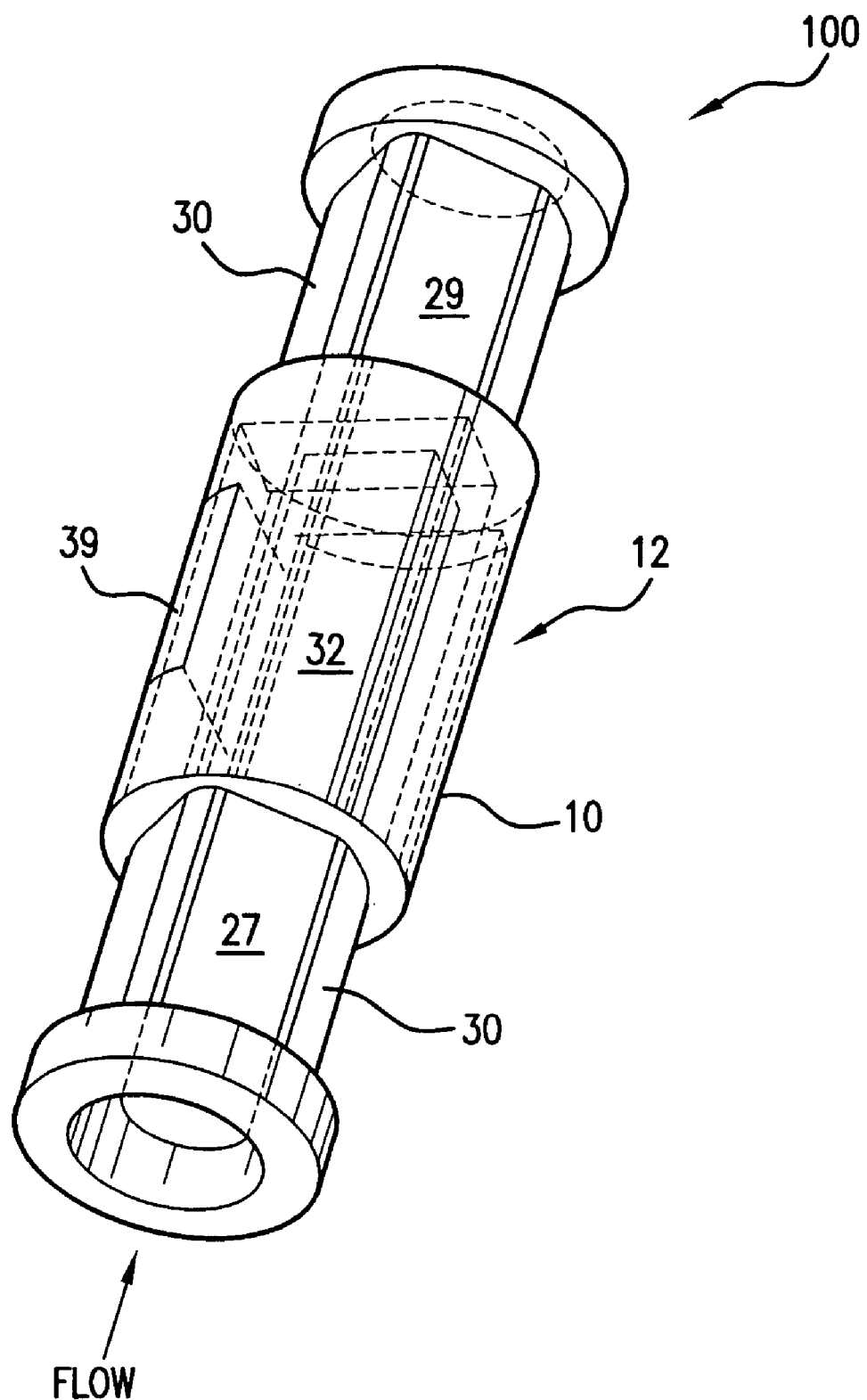
FIG. 3 is a perspective view of the device of FIGS. 1(a)–1(c).
Figure 4C:
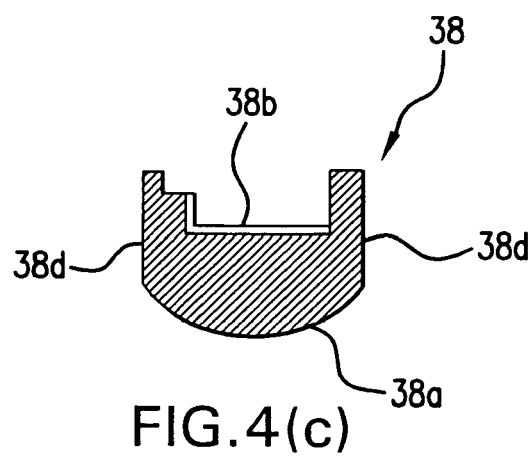
FIGS. 4(a)–4(d) are a plan view, side view, and cross sectional end views, respectively, of a cap portion for use with the device of FIGS. 1(a)–1(c).
Figure 4A:
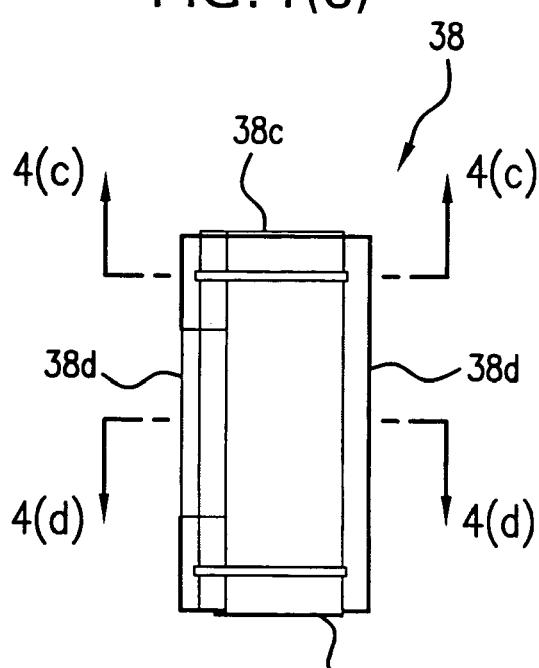
Figure 4B:
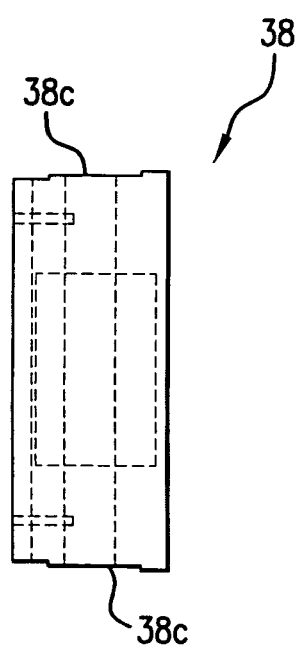
Figure 4D:
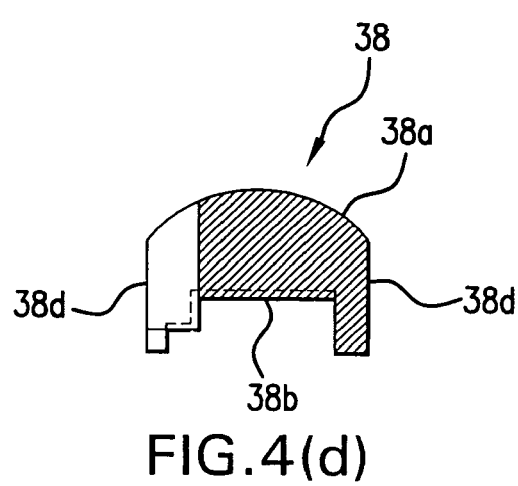
Figure 5B:
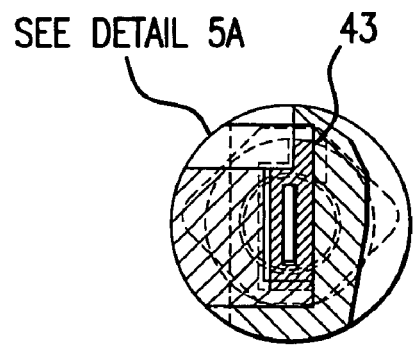
FIGS. 5(a)–5(b) are cross sectional end views and an enlarged detail of the device of FIGS. 1(a)–1(c).
Figure 5A:
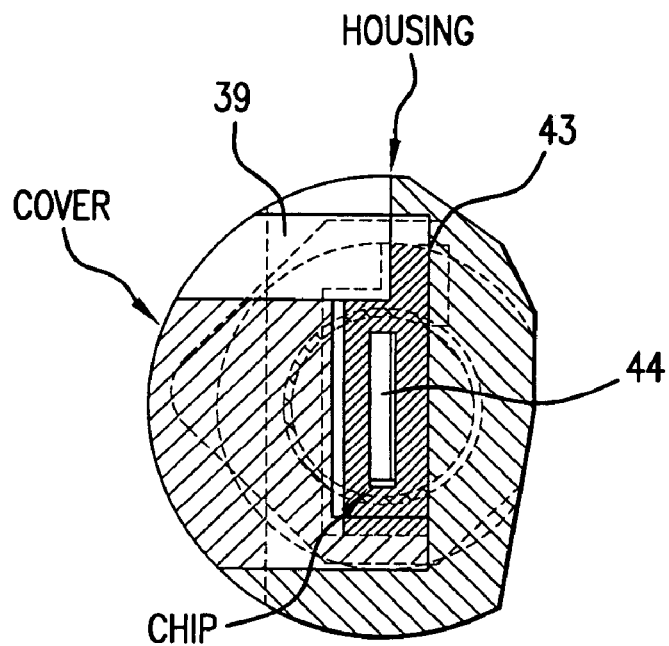
Figure 9:
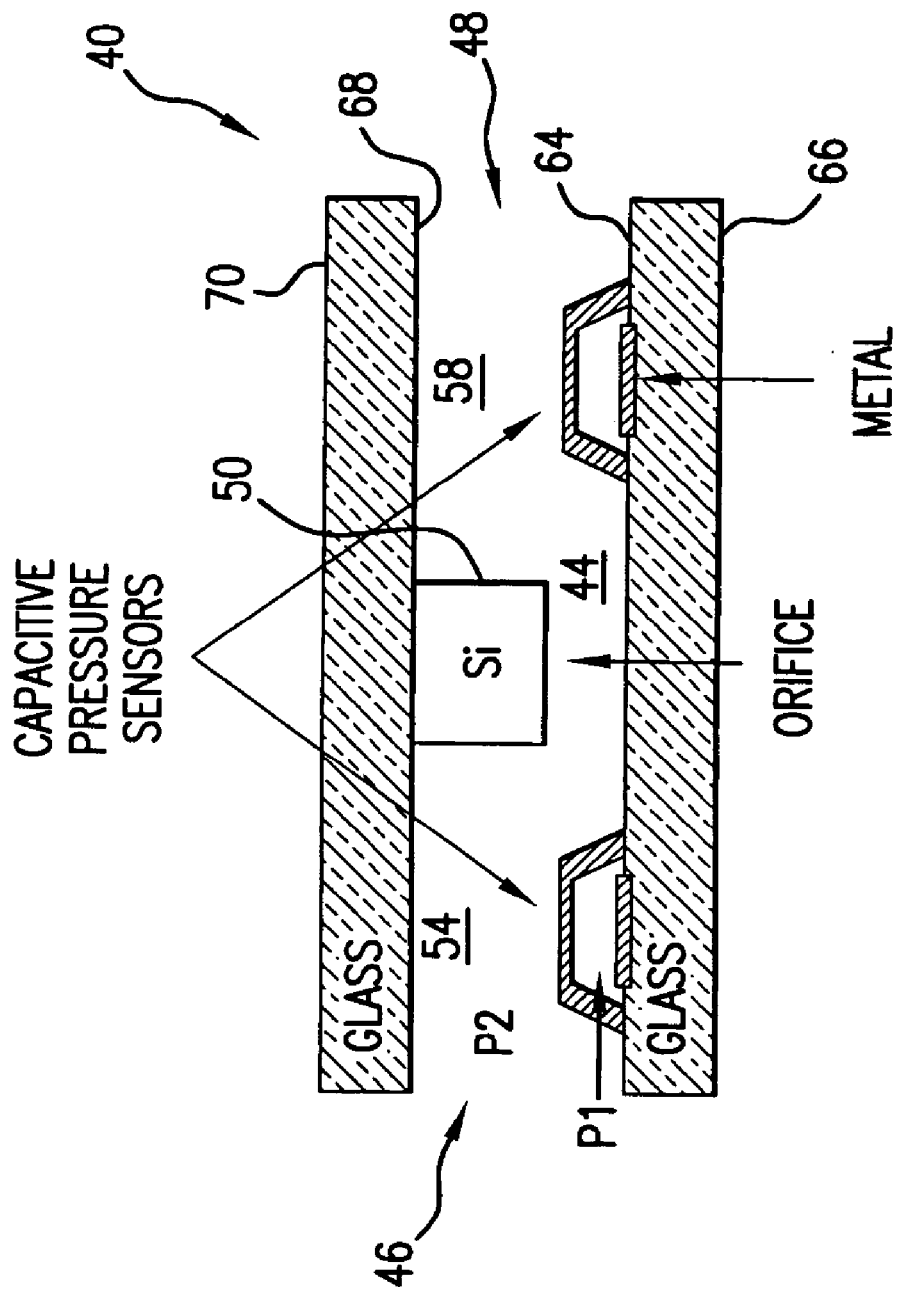
FIG. 9 is a schematic view of a sensor assembly portion of the device for obtaining flow rate measurements in accordance with the invention.
Figure 10:
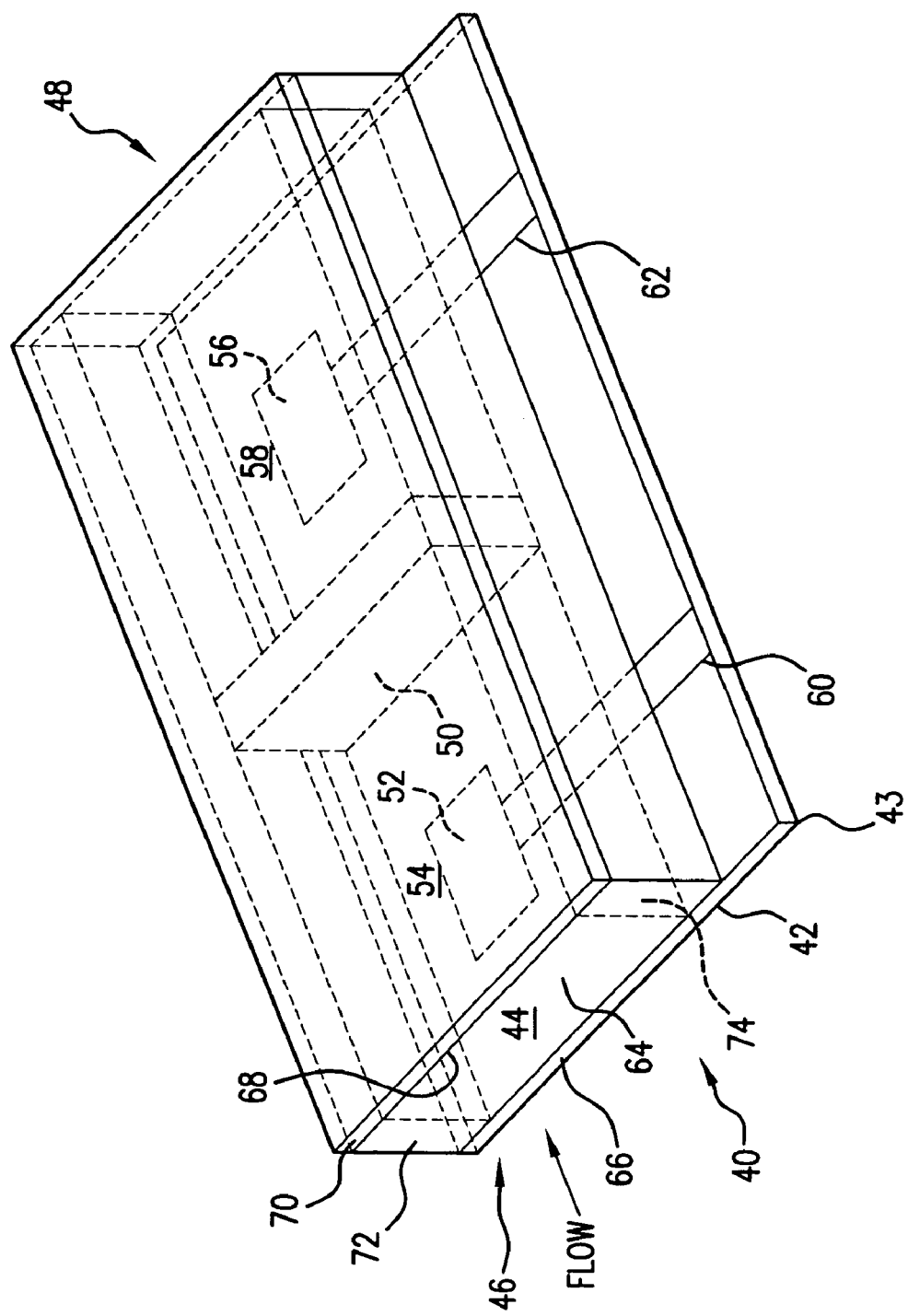
FIG. 10 is a perspective schematic view of a sensor assembly portion of the device in accordance with the present invention.

For example, and for purpose of introduction only, FIGS. 1–6 show a flow sensor device 100 for obtaining flow characteristics in accordance with the invention. FIGS. 9–10 show a sensor assembly 40 including a flow restricting element 50, an upstream fluid pressure sensor 52 and a downstream fluid pressure sensor 56. FIGS. 1–3 show one embodiment of a housing 10 for the sensor assembly 40 of the device. Alternative embodiments or variations of the device, such as shown in FIGS. 7–8, also are suitable for the present invention as will be recognized from the description below.

The flow sensor device in accordance with the invention includes a sensor assembly. The sensor assembly generally includes a first fluid flow passage having an upstream pressure sensor and a downstream pressure sensor separated by a flow restricting element.

For purposes of illustration and not limitation, the sensor assembly 40 is schematically depicted in FIGS. 9–10. FIG. 9 shows a side view representation of the sensor assembly 40, while FIG. 10 shows an isometric view of the sensor assembly 40. The sensor assembly 40 includes a body 42 defining a first fluid flow passage 44 having an inlet 46, an outlet 48 and a flow restricting element 50 located along the first flow passage 44 between the inlet 46 and the outlet 48. As shown in FIG. 10, a registration extension 43 provides registration between housing 10 and sensor assembly 40 as will be discussed. (See also FIGS. 5(a)–5(b), 7(d)–7(e), 8(d)). As embodied herein, the sensor assembly 40 also includes an upstream fluid pressure sensor 52 to sense an upstream fluid pressure at an upstream location 54 in the first fluid flow passage 44 between the inlet 46 and the flow restricting element 50. The sensor assembly 40 also includes a downstream fluid pressure sensor 56 to sense a downstream fluid pressure at a downstream location 58 in the first fluid flow passage 44 between the flow restricting element 50 and the outlet 48. At least one upstream signal contact 60 is connected to the upstream fluid pressure sensor 52, and at least one downstream signal contact 62 is connected to the downstream fluid pressure sensor 56. Preferably, the signal contacts 60, 62 are located on the registration extension 43 for accessibility, as will be discussed.

In accordance with one aspect of the invention, the sensor assembly can be constructed as an independent component, such that the body is constructed of one or more walls as depicted in FIG. 10. As embodied herein, the upstream pressure sensor 52 and downstream pressure sensor 56 are preferably formed on a first inner surface 64 of a first wall 66 of the body 42. The first inner surface 64 is substantially planar. The device further includes a second inner surface 68 of a second wall 70 that, as embodied herein, is also substantially planar. As embodied herein, third wall 72 and fourth wall 74 are also provided to space apart first wall 66 and second wall 70. Collectively, the first wall 66, second wall 70, third wall 72 and fourth wall 74 of the sensor assembly 40 cooperate to define the first fluid flow passage 44 therebetween. First wall 66 and second wall 70 are preferably formed of glass or similar suitable substrate. Third wall 72 and fourth wall 74 are preferably made from silicon or the like, and can be formed on first wall 66 and/or second wall 70 using photolithographic deposition and/or chemical etching or ion bombardment techniques as are well-known to those of skill in the art. Upstream pressure sensor 52 and downstream pressure sensor 56 of the preferred embodiment are capacitance-type pressure sensors disclosed, for example, in U.S. Pat. No. 6,445,053 titled "Micro-Machined Absolute Pressure Sensor," the disclosure of which is expressly incorporated by reference herein. Pressure sensors of this type are employed in a flow measurement device disclosed in U.S. Pat. No. 6,349,740, titled "Monolithic High-Performance Miniature Flow Control Unit," the disclosure of which is also expressly incorporated by reference herein.

In accordance with an alternative embodiment of the invention (not shown), the upstream pressure sensor 52 and downstream pressure sensor 56 need not be located in the first flow passage 44. For example, pressure sensors 52, 56 can be located externally to the first fluid flow passage 44 but in fluid communication with upstream location 54 and downstream location 58 by way of pressure taps and/or fluid lines (not shown) or the like. In further accordance with this alternative embodiment of the invention it is possible to form the body as part of housing to define the first flow passage 44 with flow restricting element 50. In this manner, the body of the sensor assembly can be formed, as will be discussed, during the insert molding process rather than providing a separate component.

A variety of alternative configurations and structures can be used for upstream pressure sensor 52 and downstream pressure sensor 56. While capacitance-type pressure sensors are depicted herein, it is also possible to use other forms of differential pressure measurement. This is particularly applicable if pressure sensors 52, 56 are not internal to fluid flow passage 44. In accordance with this alternative aspect of the invention, measuring the pressure difference between upstream location 54 and downstream location 58 can be achieved by any one of a number of ways.

For example, if pressure taps (not shown) are provided at upstream location 54 and downstream location 58 connected to pressure transmission lines (not shown), each pressure transmission line can be connected to opposite ends of a differential pressure measurement device. Such devices can include, for example, a liquid-filled manometer. Alternatively, a diaphragm having one or more electrically conductive elements disposed therein can be used to sense a differential pressure. In accordance with this aspect of the invention, each of the upstream pressure sensor 52 and downstream pressure sensor 56 can be recognized as each of two inputs to the differential pressure measurement device.

As previously noted, and in accordance with the present invention, a flow restricting element is located along the first fluid flow passage between the inlet and outlet. With reference to FIGS. 9–10, flow restricting element 50 is formed on the first inner surface 64 and/or on the second inner surface 68. The flow restricting element 50 is sufficiently sized and shaped to provide a proportionately large pressure drop in a flow passing through the first fluid flow passage 44 over a relatively short distance, as compared to a flow passage not having such a flow restricting element. In this preferred embodiment, flow restricting-element 50 is preferably formed by depositing a semiconductive material such as silicon on the first inner surface 64 and/or the second inner surface 68. Flow restricting element 50 can be formed integrally with first wall 66 and/or second wall 70, or separately as an insert. Similarly, flow restricting element 50 can be provided with a variety of alternative configurations, such as an orifice deferred through a wall or the like.

A variety of structures can be used for the structure of sensor assembly 40. For example, pressure sensors 52, 56 can be provided on a glass substrate, which in turn is positioned in a first fluid flow passage that is molded in the housing as a whole. Alternatively, and as previously discussed, a first fluid flow passage 44 could be provided that is molded into housing 10 having pressure taps and lines in fluid communication with the pressure sensors 52, 56. In accordance with this alternative aspect of the invention, first fluid flow passage 44 could be provided in cylindrical form. Flow restricting element 50 could likewise be provided in the form of an orifice that is placed in the first fluid flow passage 44 or integrally formed therewith. The sensor assembly 40 can be monolithic, having the flow-restricting element 50 and the pressure sensors 52, 56 in an integrated structure. A monolithic sensor assembly may reduce the assembly cost and the size of the sensor assembly.

In accordance with the present invention, the flow sensor device further includes a housing for the sensor assembly. The housing is configured to contain and protect the sensor assembly, as well as ensure proper installation within a fluid flow system.

For example and not for purposes of limitation, FIGS. 1(a)–1(c) depict a housing 10 as embodied herein. The housing 10 has a central portion 12 within which a sensor assembly 40 is contained. Housing 10 defines an upstream port 14 at an upstream end 16 of housing 10 and a downstream port 18 at a downstream end 20 of housing 10.

Furthermore, and as embodied herein, the housing 10 also includes an upstream portion 26 and a downstream portion 28. As depicted herein, and in accordance with the invention, upstream portion 26 defines upstream port 14 and downstream portion 28 defines downstream port 18. Although any of a variety of suitable configurations can be used, the ports embodied herein each includes a cylindrical bore that tapers to a narrow rectangular cross section proximate to central portion 12 so as to define upstream flow passage 27 and downstream from passage 29, respectively.

In a preferred embodiment of the invention an upstream connector 15 is located proximate the upstream port 14 and a downstream connector 19 is located proximate the downstream port 18. Each connector can be provided as a flange to mate with a corresponding flange of the fluid flow system; however alternative connector embodiments are contemplated if desired. For example, Luer connectors, threaded connections or snap fit connectors also can be used, among others. The geometry of the housing 10 and connectors 15, 19 is configured to provide a seal that is adequate to prevent leakage of liquid or gaseous fluids.

Further in accordance with the present invention, the housing is provided with at least one registration surface configured to ensure proper registration of the flow sensor device with the fluid flow system. Particularly, it is beneficial to ensure the inlet for a sensor assembly is registered with the upstream side (i.e. fluid source) of the fluid flow system, while the outlet of the sensor assembly is registered with the downstream side of the fluid flow system.

Figure 7A:
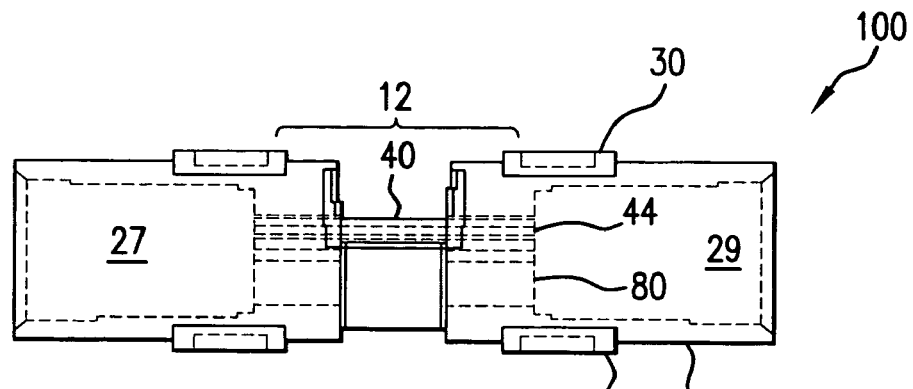
FIGS. 7(a)–7(e) are a side view, a plan view and section views of a second representative embodiment of a flow measurement device in accordance with the present invention after a first stage of a manufacturing process.
Figure 7B:
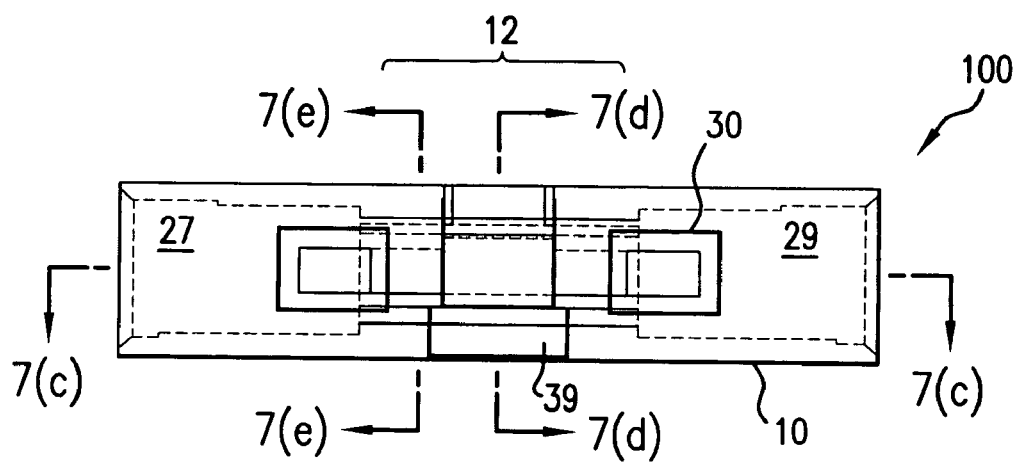
Figure 7C:
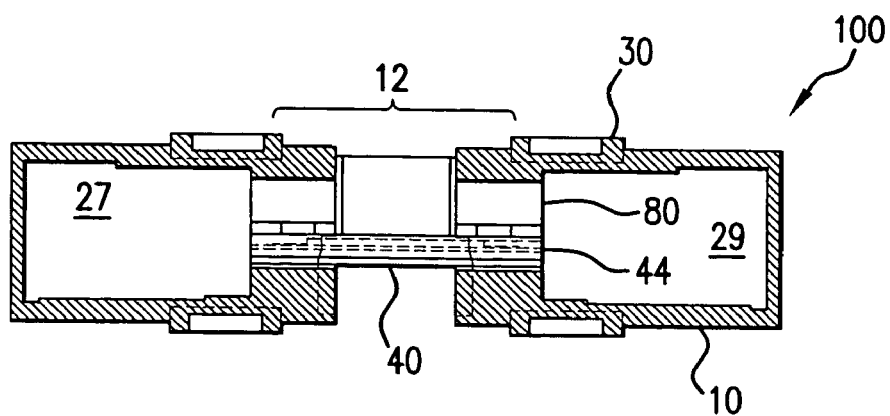
Figure 7D:
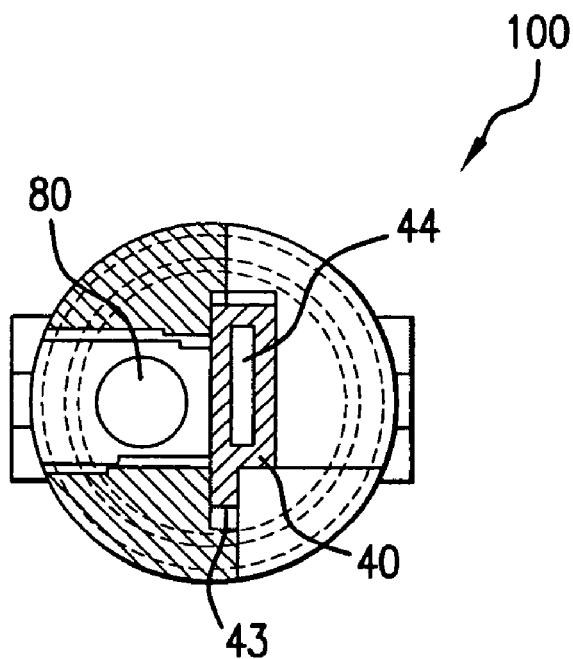
Figure 7E:
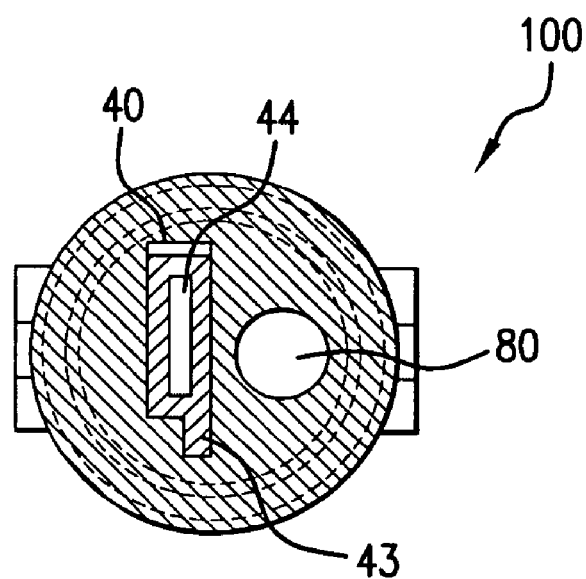
Figure 8A:
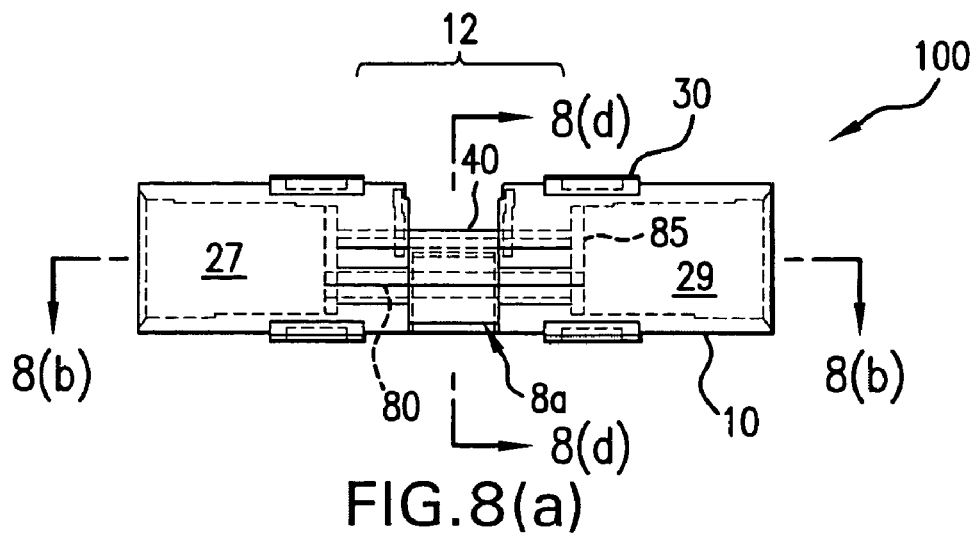
Figure 8B:
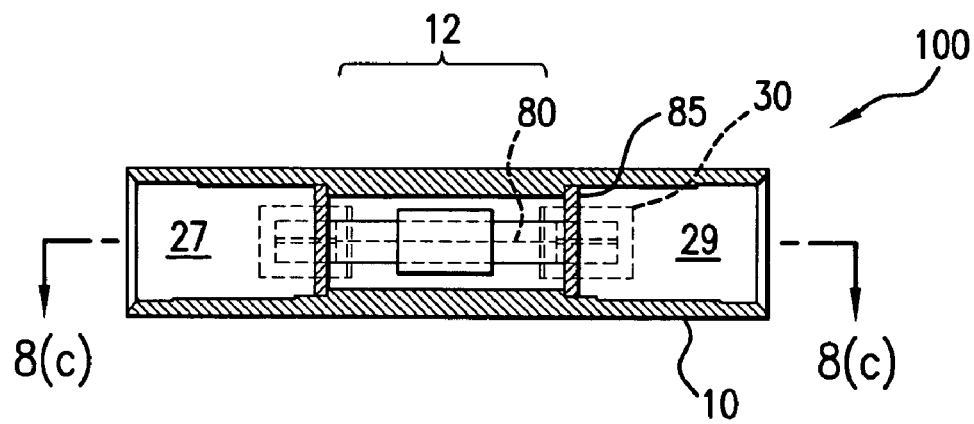
Figure 8C:
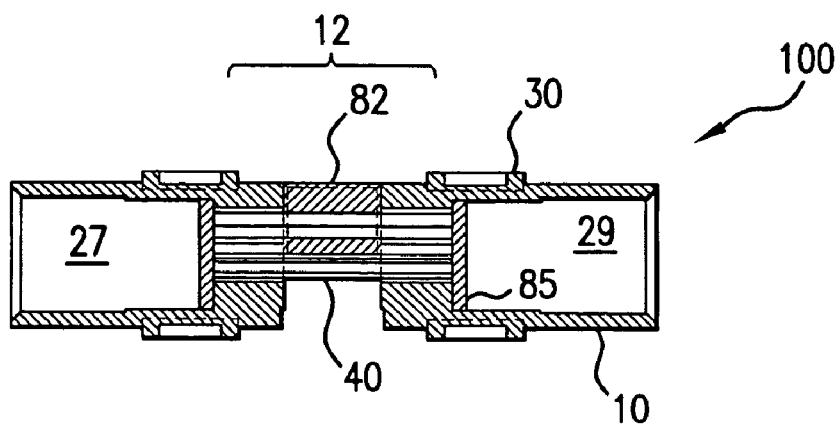
Figure 13:
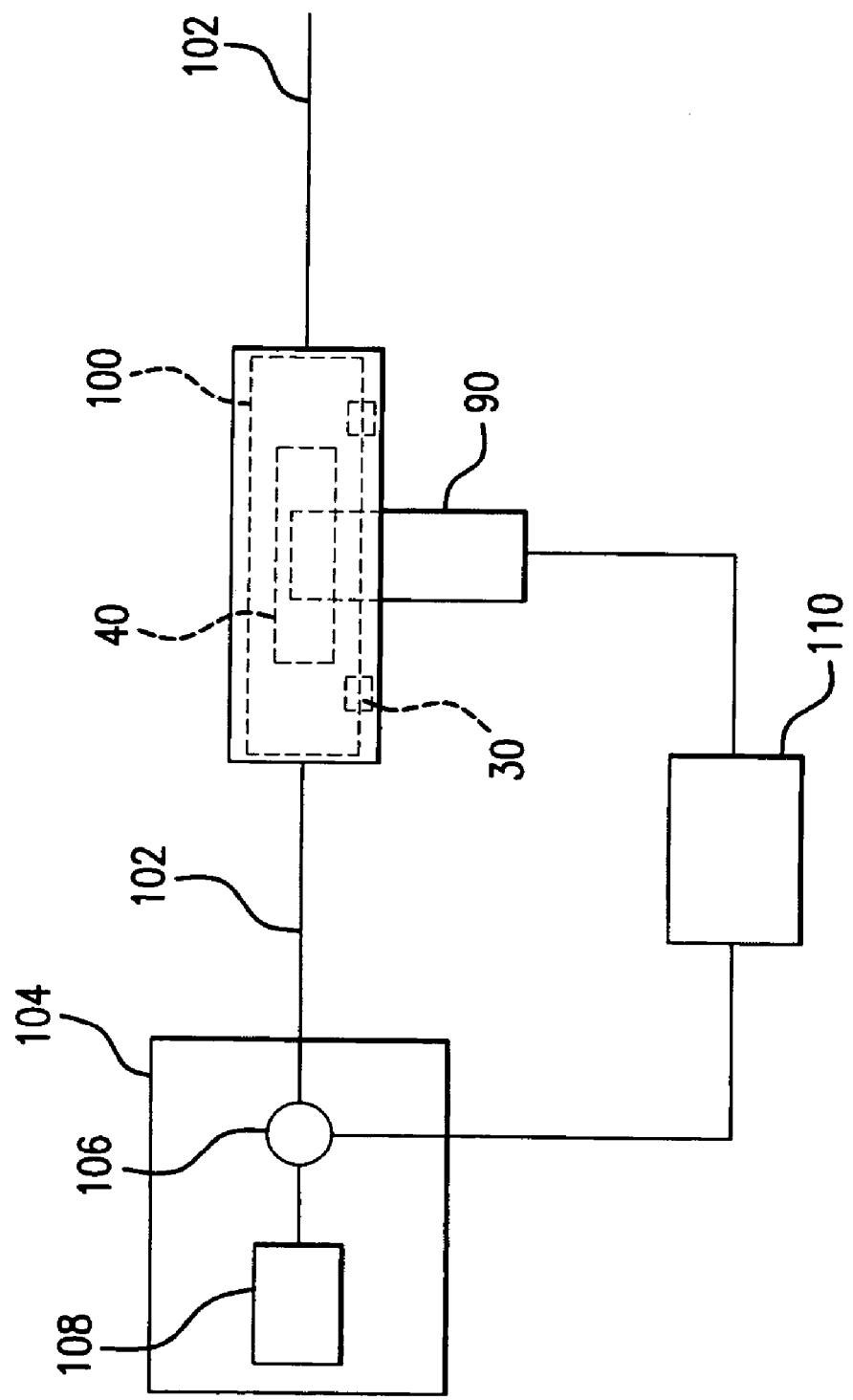
FIG. 13 is a schematic representation of a fluid flow system in accordance with the present invention.

For purpose of illustration and not limitation, as embodied herein in FIG. 1(a), each of upstream engaging portion 22 and downstream engaging portion 24 is provided with one or more registration surfaces 30. Registration surfaces 30 are configured to provide alignment between housing 10 and a fluid flow system as depicted in FIG. 13. When the device 100 is used, registration surfaces 30 ensure that the upstream port 14 is properly aligned with a fluid source. As depicted in FIG. 1(a), each registration surface 30 can be provided as a planar surface specifically angled to mate with a corresponding planar surface, or any of a number of alternative configurations, such as a protrusion, a key or a detent as shown in FIG. 7(b), provided on the fluid flow system. A registration surface 30 can be provided anywhere on the surface of the housing 10. For example, a single registration surface can be provided if asymmetrical in shape or location. If registration surfaces 30 are provided in both an upstream location and a downstream location of housing 10, the shape of each registration surface 30 will be different to prevent installing device 100 backwards into a flow system.

Figure 6:
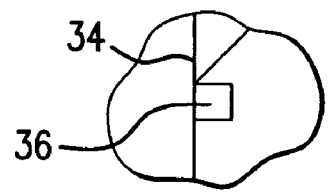
FIG. 6 is an enlarged view of a selected portion of the device for obtaining flow rate measurements of FIGS. 1(a)–1(c).

In accordance with one aspect of the invention, and as depicted in FIGS. 1(b), 1(a) and 2(b), the central portion 12 of the housing 10 defines a cavity 32 of predetermined shape. As embodied herein, for purpose of illustration and not limitation, cavity 32 is rectangular in shape. The sensor assembly 40, which will be described in detail below, has a shape and size corresponding with that of cavity 32. In this manner, the housing can be fabricated separate from the sensor assembly if desired, and then later installed. Furthermore, the cavity and sensor assembly can be provided with corresponding asymmetric shape to ensure a single orientation between the two components. The sensor assembly can be held within the cavity by a variety of mechanisms, including snap-fit configurations or similar mechanical connection. As a preferred embodiment, an adhesive, a bond or a weld material can be used. Cavity 32 preferably has at least one surface 34 that is provided with one or more recesses 36. As depicted in FIG. 6, recess 36 is sized to receive a predetermined amount of such material, such as adhesive, to hold sensor assembly 40 within cavity 32.

For purposes of illustration and not limitation, as embodied herein in FIGS. 1(a) and 4(a)–4(d), cavity 32 is further configured to receive a cap 38. Cap 38 also has a shape and size corresponding to that of cavity 32. Cap 38 has a superior face 38a, an inferior face 38b, end walls 38c and side wall portions 38d. Cap 38 is placed into cavity 32 after the sensor assembly 40 has been inserted, such that inferior face 38b is adjacent sensor assembly 40. Alternatively, sensor assembly 40 can first be affixed to inferior surface 38b of cap 38, and then installed into cavity 32. As seen in FIG. 1(a), when fully inserted into cavity 32, cap 38 has an external profile similar to that of the housing 10.

In accordance with yet another aspect of the invention, the cavity and cap can be used in combination to define the first fluid flow passage of the sensor assembly. For example, the upstream and downstream fluid pressure sensors 52, 56 can be mounted on a suitable substrate, such as glass, which is positioned within the cavity. With the sidewalls of the cavity defining side walls of the first fluid flow passage 44, the cap is positioned in the cavity and appropriately spaced from the sensors 52, 56 to complete the fluid flow passage 44. If desired the flow restricting element can be formed on the inferior surface 38b of the cap, or provided as a separate element.

Housing 10 preferably is made of a plastic that is injection-molded inside a molding cavity. Particularly, the housing can be made from acrylic, Cryolite, or a composite fiber-reinforced material, although any other suitable material-including metals and ceramics, can be used. If plastic is used the housing 10 is preferably formed by liquid injection insert molding. As is known in the art, insert molding for a hollow member generally involves using removable inserts within a molding cavity to prevent the flow of liquid plastic materials into preselected volumes within the cavity in order to define voids in the finished article. It is recognized, however, that alternative techniques, such as milling or machining, can be used if desired.

An advantage of the housing 10 depicted, for example, in FIG. 1(a), is that it can be manufactured generally by a single injection of plastic material into a mold. In this manner, inserts or "slides" are provided in a molding cavity to define voids to be created for cavity 32, upstream flow passage 27 and downstream flow passage 29. Next, liquid plastic material is injected into the mold, filling all open spaces. After hardening, the slides are removed and housing 10 is removed from the mold. The end result is a housing 10 as depicted in FIG. 3. The cavity 32 provided in this first representative embodiment of housing 10 enables the sensor assembly 40 to be installed in housing 10, as described above, followed by installation of cap 38 as depicted in FIG. 1(a). Cap 38 is also preferably made from an injection-molded plastic material such as Cryolite or acrylic, but can also be made from other plastic materials, composite materials or metal, if desired.

In further accordance with the invention, the housing defines a probe access port configured to provide access of a probe to at least one of the upstream signal contact and downstream signal contact.

For purposes of illustration and not limitation and with specific reference to FIGS. 1(a), 3, 5 and 14, as embodied herein, probe access port 39 is defined by a gap between cap 38 and sensor assembly 40. Probe access port 39 provides access of a probe 90 to at least one of upstream signal contact 60 or downstream signal contact 62, and preferably to both, on surface 43. The physical geometry of probe access port 39 provides alignment between signal contacts 60, 62 and an external probe 90 as discussed below. Generally, however, probe access port 39 can be of any desired configuration that provides suitable registration between signal contacts 60, 62 and probe 90.

Particularly, and in accordance with another aspect of the inventions, the probe access port 39 has a shape and size corresponding to a predetermined shape and size of the probe to ensure proper alignment of the probe with the corresponding contacts 60, 62. A preferred embodiment includes using a wedge shape for the predetermined shape of the connector body of the probe 90 and corresponding port 39. The contacts 60, 62 are located on the proximate port 39, the apex of the wedge shape, and the leads 92 of probe 90 are located on the apex of the connector body. In this manner, the angled surfaces of the wedge shapes interact to align more accurately the leads 92 with the contacts 60, 62 as shown in FIG. 14. Thus, contact is made between probe 90 and one longitudinal surface 39a and one radial surface 39b that define probe access port 39 within housing 10 that provides for adequate force to assure contact between leads 92 on probe 90 and contacts 60, 62 on sensor assembly 40. These electrical contacts are preferably in close proximity to registration surfaces 30 on the outside of housing 10 that are engaged with external clamp assembly 120 that is also preferably referenced to the probe 90 (See FIGS. 15(a)–15(c)).

A variety of different configurations can be used for probe access port 39. Port 39 can alternatively be slot-shaped or can take other forms, so long as the geometry of housing 10 provides for registration and alignment between signal contacts 60, 62 and leads 92 on probe 90.

In accordance with another aspect of the invention, the housing can further define a second fluid flow passage between the upstream port and downstream port of the device.

For purposes of illustration and not limitation, FIGS. 7(a)–7(e) and 8(a)–8(h) show a second exemplary embodiment of a flow measurement device in accordance with the invention. As embodied herein, housing 10 includes a second fluid flow passage 80. The second fluid flow passage 80 provides a flow path that is arranged for fluid communication in parallel to the first fluid flow passage 44 between the upstream port 14 and the downstream port 18. In this manner, second fluid flow passage can act as a bypass line in combination with first fluid flow passage. The embodiment is particularly beneficial when increased fluid flow is required past the flow restricting element of the sensor assembly.

Preferably, a valve is provided in operative communication with the second fluid flow passage for selective fluid flow therethrough. Any of a variety of suitable valve configurations can be provided. In a preferred embodiment, however, and as shown in FIG. 8, the valve is formed of a compressible wall member 82 of the second fluid flow passage 80. The compressible wall member 82 is preferably formed from an elastomeric material such as silicone.

The second fluid flow passage 80 further has a first transverse dimension 84 and a second transverse dimension 86 perpendicular to the first transverse dimension. (See FIG. 8(e)). As embodied herein, the first transverse dimension 84 is smaller than the second transverse dimension 86, such that the cross section of the second fluid flow passage has an ellipsoidal shape with a small radius at each apex 87 (See FIGS. 8(d), 8(e), 8(h)). In this manner, the compressible wall member 82 is more readily compressed upon the application of a force aligned with the first transverse dimension, than if the second fluid flow passage had a circular cross section. Moreover, the small radius of each apex 87 ensures that the second fluid flow passage can close with a minimal applied force.

It is noted that a modified manufacturing process is used when forming a device in accordance with the second representative embodiment of the invention of FIGS. 7(a)–7(e) and FIGS. 8(a)–8(h). When forming a housing 10 with a compressible wall member 82, the housing 10 is formed in distinct manufacturing steps.

To make the embodiment of housing 10 depicted in FIGS. 7, 8, 11 and 12, the sensor assembly 40 preferably is first placed between slides within a mold, wherein the slides define voids to be created for second fluid flow passage 80 and surrounding elastic wall member 82, upstream flow passage 27, downstream flow passage 29 and the probe access port 39. Next, the desired liquid plastic material is injected into the mold, filling all open spaces as described above. After hardening, the housing has a form as depicted in FIGS. 7(a)–7(e). The slide(s) defining the voids to be created for second fluid flow passage 80 and surrounding elastic wall member 82 are replaced with smaller slide(s) corresponding to the size and shape of second fluid flow passage 80. As embodied herein, an elongate slide with an elliptical cross section with a small radius at the apex 87 can be used. The slides defining upstream flow passage 27 and downstream flow passage 29 are also retracted slightly, to create disc-shaped voids in the upstream flow passage and downstream flow passage 29 near central portion 12. Next, a suitable liquid elastomeric resin is injected into the voids to form the elastic wall member 82 of second fluid flow passage 80, and disc-shaped seals 85 in the upstream flow passage and downstream flow passage 29 near central portion 12. After the elastomeric material cures, housing 10 is removed from the mold. The structure that results from this manufacturing process is depicted in FIGS. 8(a)–8(h). Seals 85 can assist in providing a liquid and gaseous seal between device 100 and a fluid flow line 102.

Figures 11A, 11B:
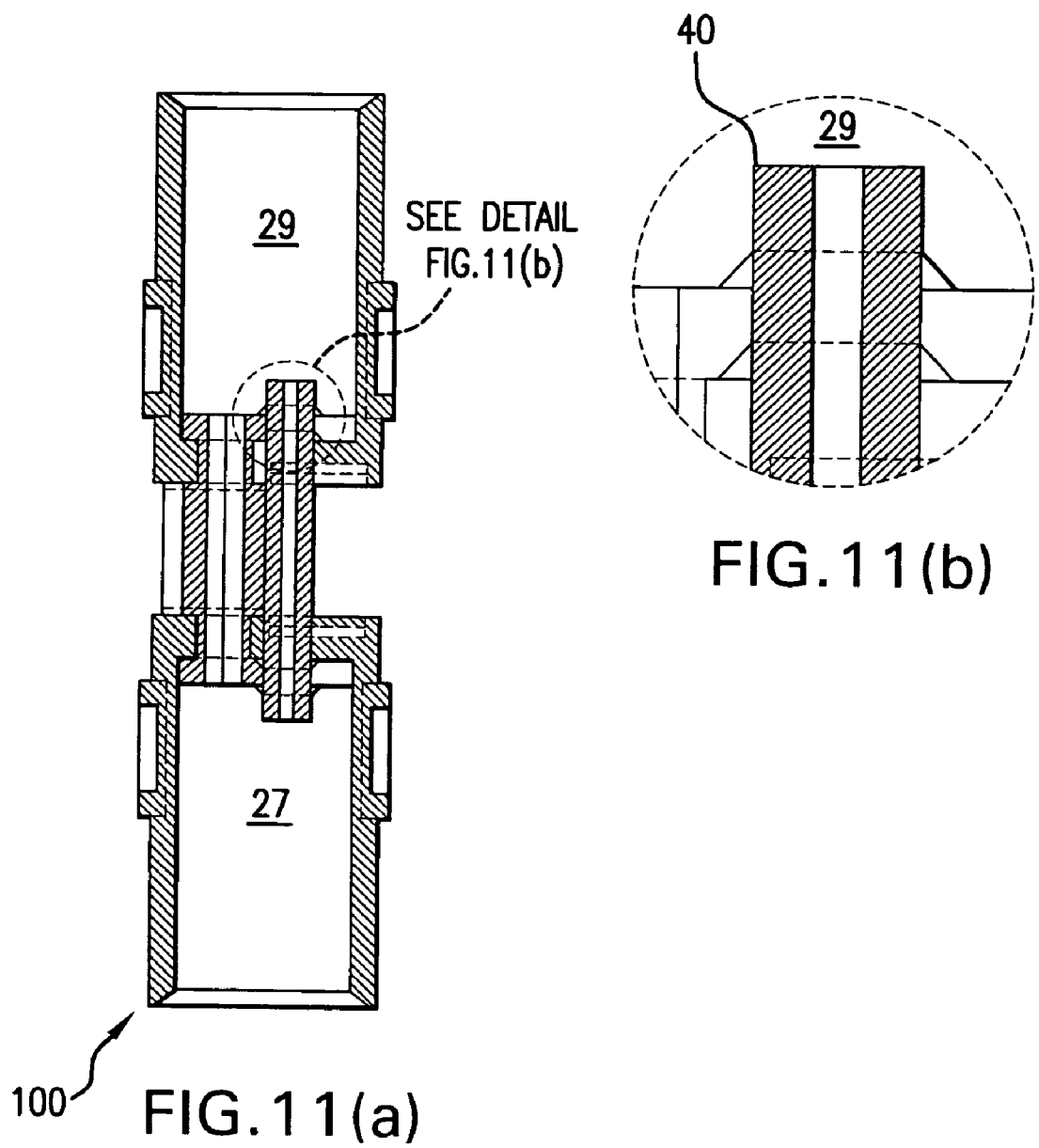
FIGS. 11(a)–11(b) are a cross-sectional side view and an enlarged detail view, respectively, of the device of FIGS. 7(a)–7(e) in accordance with the present invention.
Figure 12:
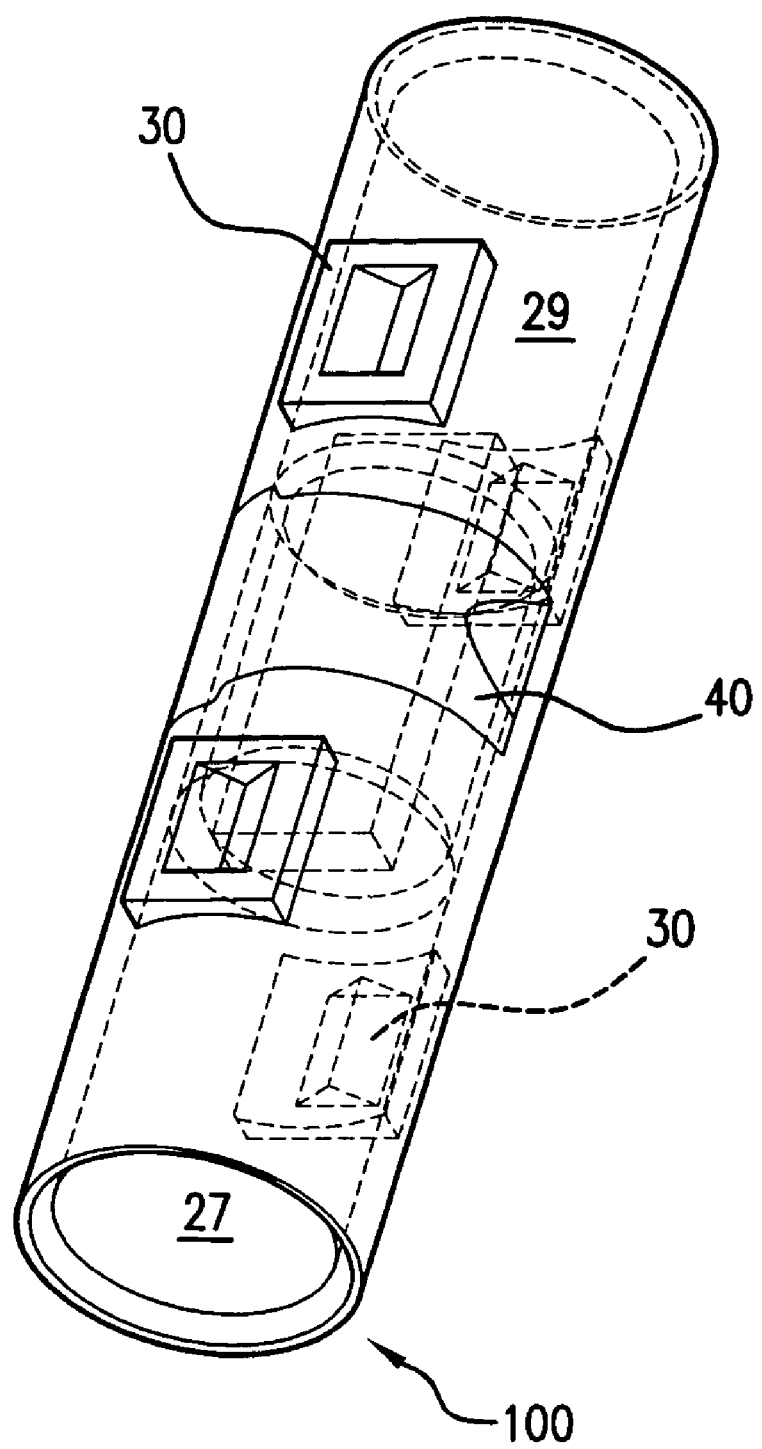
FIG. 12 is a perspective view of the device of FIGS. 7(a)–7(e) in accordance with the present invention.

As further depicted in FIGS. 11(a)–11(b), the sensor assembly can be secured with the housing so as to protrude into flow passages 27, 29. This facilitates the manufacturing process, since slides will generally be used to hold sensor assembly 40 in position during the manufacturing process. As an alternative however, the sensor assembly can be positioned subsequently within a cavity formed in the housing in a manner similar to that described with regard to FIGS. 1–3 above if desired.

In accordance with another aspect of the invention, a fluid sensor system is provided. The system includes a device for obtaining flow characteristics as described above as well as a probe to receive signals representative of a fluid flow characteristic and a processor to process signals from the probe.

For purposes of illustration and not limitation, as embodied herein and with reference to FIG. 13, a system is depicted schematically including flow measurement device 100 in accordance with the invention as described above in combination with a probe 90 and a processor 110.

As previously discussed, one aspect of the invention includes providing the probe with a connector body having a predetermined shape wherein the probe access port of the housing has a corresponding shape to ensure proper alignment of the probe with at least one of the upstream signal contact and downstream signal contact.

For example, and as embodied herein, probe 90 has a wedge-shaped connector body that corresponds to the shape of probe access port 39 as depicted in FIG. 14. Advantageously, the geometry of probe access port 39 (perimeter of opening indicated by dashed lines) eliminates any need for a lead frame to provide registration between probe 90 and sensor assembly 40.

Particularly probe 90 includes a connector body 95 having a plurality of leads 92 that are connected to a processor as discussed below. With reference to FIG. 14, the corresponding shapes of probe access port 39 and connector body ensure proper registration between contacts 60, 62 on the sensor assembly 40 with leads 92 on the probe 90. Preferably, the geometric tolerance between probe 90 and probe access port 39 is sufficiently small to permit probe 90 to be press-fitted or snap fitted into probe access port 39. Leads 92 can be further configured to wipe across contacts 60, 62 while being inserted as depicted in FIG. 14. Providing a wiping action ensures a stable fit and good electrical contact between leads 92 and contacts 60, 62. Thus, as discussed above, contact is made between probe 90, surface 39a and surface 39b to provide for adequate force to assure contact between leads 92 on probe 90 and contacts 60, 62 on sensor assembly 40. The purpose of this is to assure precision in locating the multiple contacts 92 on probe 90 with the contacts 60, 62 on sensor assembly 40. The fit between leads 92 and contacts 60, 62 must be secure to ensure a connection that does not generate excessive noise that would reduce the sensitivity of the system. Contacts 60, 62 are preferably made of gold, although other suitable electrically conductive materials can be used.

Probe 90 is preferably a flexible printed circuit element. More preferably, the probe includes a plurality of signal leads 92 located between two or more conductive shield layers 96 that are insulated from the signal leads 92 to minimize noise. The signal leads 92 defined by the flexible printed circuit element will further define or separately include a spring element for enhanced contact. To prevent damage to the spring based leads 92, however, the connector body 95 is configured to prevent over bending of the leads beyond an established limit. This is accomplished by containing the leads within a gap 98 of sufficient clearance defined in the connector body 95, as shown in detail of FIG. 14(a). The connector body of the probe can be over molded of any suitable material, such as plastic or elastomeric, or formed by alternative known techniques, to protect the signal leads.

A variety of alternative configurations and structures can be used for probe 90. For example, although probe 90 is depicted herein as a single flexible printed circuit element, a plug (not shown) with a plurality of conductive prongs can be used, wherein the probe access port 39 is defined by a plurality of passages (not shown) through housing 10 configured to provide registration between electrical contacts 60 on sensor assembly 40 and the plurality of conductive prongs on probe 90.

In accordance with a further aspect of the invention, the system further includes a fluid flow system comprising a fluid flow line in communication with a fluid source. As embodied herein and with specific reference to FIG. 13 for purpose of illustration, a fluid flow line 102 is provided in communication with a fluid source 104. The fluid source 104 can be a pump 106 connected to a reservoir 108. In accordance with this aspect of the invention, pump 106 is used to selectively pump fluid through the first flow passage using positive displacement of the like.

A variety of alternative configurations can be used for fluid source 104. For example, fluid source 104 can include a conventional intravenous feed reservoir, such as a bag or bottle, connected to fluid flow line 102 for gravity feed. Preferably, a control valve (not shown) is provided in series with fluid flow line 102 for control of the flow by a processor (discussed below) in response to signals from device 100 to increase or decrease the rate of flow. The pump and/or control valve can be adjusted manually or automatically.

As previously noted, the system includes a processor to process signals received by the probe. The processor can be provided in a variety of forms, such as a software program for operation on a conventional workstation, or as hardware embedded into a chip or on a hardwired device as is known in the art.

In accordance with a further aspect of the invention, the processor controls the pump in response to signals obtained by the probe from the sensors.

For purposes of illustration and not limitation, with specific reference to FIG. 13, a system is provided including a processor 110. Processor 110 can be a control circuit that is programmed to vary the flow output of pump 106 in response from signals obtained from upstream fluid pressure sensor 52 and downstream fluid pressure sensor 56 to provide a desired rate of fluid flow. Alternatively, processor 110 can be provided in the form of a computer workstation (not shown). Examples of suitable processors are a wide variety of embedded processors available from many semiconductor manufacturers such as Intel Corporation, Advanced Micro Devices, Inc. ("AMD") and Integrated Device Technology, Inc. ("IDT").

In accordance with yet a further aspect of the invention, the system can further include a locking mechanism to mate the housing with the fluid flow line. Generally, the locking mechanism at least has an unlocked condition for receipt of the housing, and a first locked condition to align the housing with the fluid flow line. In a preferred embodiment, the locking mechanism further includes a second locked condition to position the probe in the housing.

The locking mechanism can be provided in any of a variety of forms or configurations. For example, one or more lever members can be provided, each with a first condition to allow receipt of the housing 10 into communication with the fluid flow line 102, and a second condition to align and secure the housing in position. The probe 90 can be mounted on one such lever member so as to be inserted into the probe access port 39 and in communication with the contacts when the lever member is moved to its second condition.

Figure 15A:
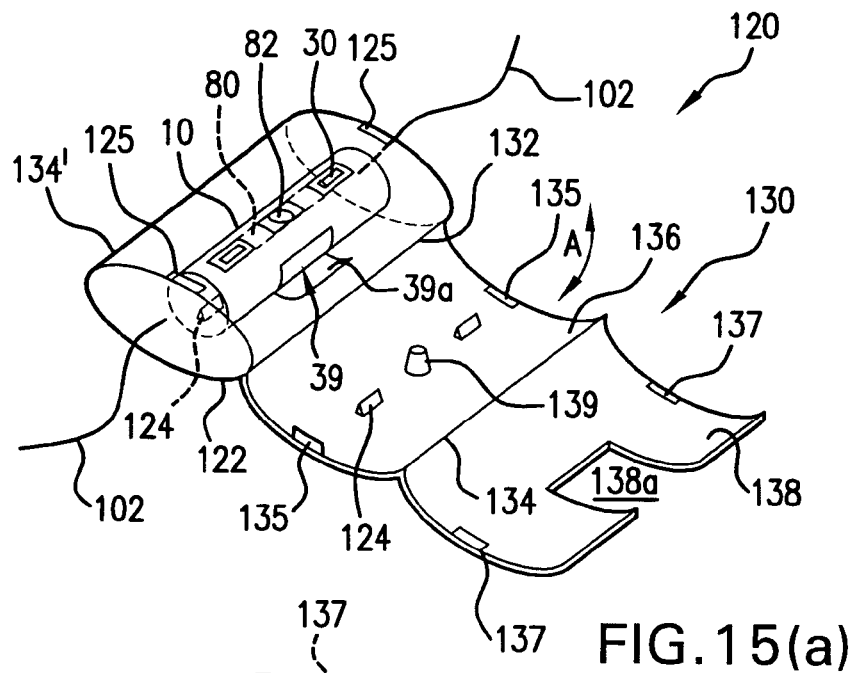
FIGS. 15(a)–15(c) are schematic views of a representative locking mechanism for use in accordance with the present invention.
Figure 15B:
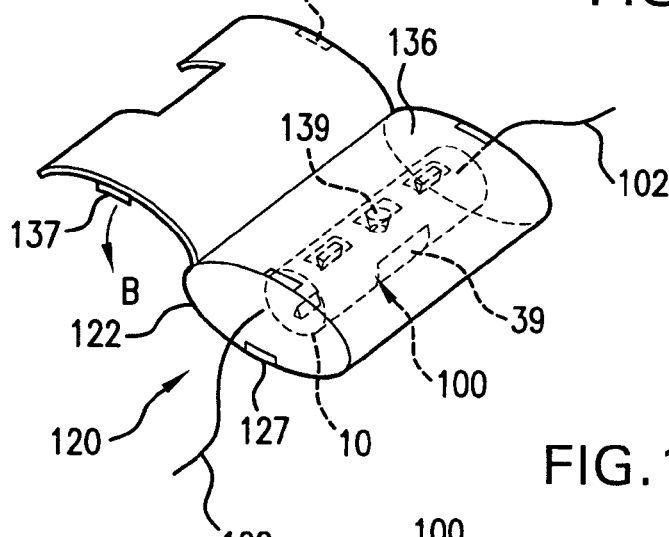
Figure 15C:
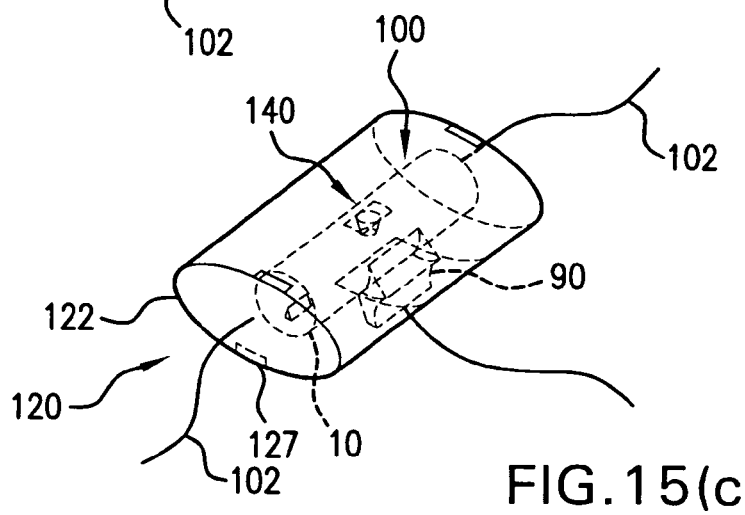

For purposes of illustration and not limitation, as further embodied herein and depicted schematically in FIGS. 15(a)–15(c), a locking mechanism 120 is provided to connect the housing with a fluid flow line 102. Locking mechanism 120 is defined by a locking body 122, and a lever member defined in this embodiment as cover 130. Cover 130 has two hinges 132 and 134. Hinge 132 connects locking body 122 with a first cover portion 136 of cover 130. Hinge 134 connects first cover portion 136 of cover 130 to second cover portion 138 of cover 130.

In an unlocked condition, as depicted in FIG. 15(a), the locking mechanism can receive flow measurement device 100. Flow measurement device 100 is placed in the locking mechanism 120 when the locking mechanism 120 is in an unlocked condition wherein cover 130 is fully open, such that registration surface 30, defined as one or more detents, mate with receiving surface 124, defined by corresponding protrusions.

Locking mechanism can be changed from the unlocked condition to a first locked condition. As embodied herein and as depicted in FIGS. 15(a)–15(b), locking mechanism 120 is changed to the first locked condition by rotating (in direction of arrow "A") first cover portion 136 of cover 130 about hinge 132 so that tabs 135 on cover 130 mate with tabs 125 on locking body 122. Preferably, a snap fit is provided, although alternative closure mechanisms can be used if desired. Thus, in the first locked condition, locking mechanism 120 holds housing 10 of flow device 100 in place in-fluid flow line 102, such that registration surface 30 on the housing 10 is maintained in alignment with receiving surface 124. Locking mechanism 120 thus ensures alignment between fluid flow line 102 and flow sensor device 100.

The locking device can further include a second locked condition. For purposes of illustration and not limitation, as embodied herein in FIGS. 15(b)–15(c), locking device 120 is changed from a first locked condition to a second locked condition by rotating second cover portion 138 (in direction of arrow "B") about hinge 134 until tabs 137 on second cover portion 138 engage with tabs 127 on locking body 122. If desired, the second cover portion 138 can be connected by a hinge to the locking body for independent operation, for example along the longitudinal edge 134' opposite hinge 132, such that first cover portion 136 and second cover portion 138 can be operated independently.

In a preferred embodiment, and as best seen from FIG. 15c, the probe is mounted to or otherwise attached to second cover portion 138, such that movement of second cover portion 138 into the second locked condition of locking mechanism advances probe 90 into probe access port 39 in housing 10. As embodied herein, second cover portion 138 defines an opening 138a that fits around and provides registration with probe 90. Second cover portion 138 can then retain probe 90 in place to ensure secure contact for making fluid flow measurements or the like.

In accordance with a further aspect of the invention, as previously described with regard to the embodiment of FIGS. 7–8, a valve can be provided for selective flow through a second fluid flow passage. The valve has a first condition to allow flow through the second flow passage and a second condition to prevent flow through the second flow passage. The system of the preferred embodiment further includes an actuator to change the valve from the first condition to the second condition when the locking mechanism is moved from the first locked condition to the second locked condition.

For purposes of illustration and not limitation, as embodied herein, the second exemplary embodiment of FIGS. 7–8 in accordance with the invention is shown in FIG. 15 having a second fluid flow passage 80. The valve includes at least a portion of the second fluid flow passage, wherein the valve is defined by a compressible wall member. As embodied herein, the second fluid flow passage 80 is, by default, in a first condition, or an open state such that fluid can be passed therethrough. After having been placed in the locking mechanism 120, it is possible to provide one of the cover portions with an actuator embodied as protrusion 139, wherein protrusion 139 presses against compressible wall member 82 of second fluid flow passage 80, so as to move the value to the second condition. As discussed above, the cross-section of second fluid flow passage 80 is preferably elliptical with a small radius at the apex. The dimension of flow passage 80 parallel to the line of force exerted by protrusion 139 is less than the dimension of flow passage 80 that is perpendicular to the line of force of protrusion 139. In this manner, relatively less force is required to compress the compressible wall member and thus close the valve. As embodied herein, protrusion 139 is a pin although alternative actuators can be used depending on the valve.

In accordance with a further aspect of the invention, if desired, second fluid flow passage 80 can be opened by opening the valve to increase flow through the flow measuring device 100. This could be accomplished by opening the appropriate cover portion or by configuring the actuator, e.g. protrusion 139, for independent movement such that it can be moved to a position where it does actuate the valve.

A variety of structures can be used for the protrusion 139. For example, a spring-loaded pinch valve (not shown) can be used. Alternatively, the second fluid flow passage 80 can be made of an elastic material that is biased to remain closed, whereby the resistive force of the passage can be overcome by an increase in fluid pressure or by application of a lateral force to open the elliptical passage. Additionally or alternatively, a frangible membrane (not shown) can be provided, to initially block the second fluid flow passage 80, which in turn could be ruptured by an actuator or by a pressure surge should it become necessary to deliver a significant amount of beneficial agent to a patient through device 100 in a relatively short amount of time.

In further accordance with the invention a method is provided for obtaining flow characteristics of a fluid flow system. The method includes providing a device described above; directing a fluid flow through the first fluid flow passage; obtaining a signal corresponding to the fluid pressure in the first fluid flow passage at the locations of the upstream fluid pressure sensor and the downstream fluid pressure sensor; and determining a flow characteristic based upon the signal. The method has been described in detail in conjunction with the device and system of the invention.

As embodied herein and with reference to FIGS. 9 and 10, a fluid can be flowed through first fluid flow passage 44 by applying a differential fluid pressure across the inlet 46 and outlet 48 of the sensor assembly 40. When fluid flows through the first flow passage 44, a different pressure reading is detected at an upstream location 54 than at a downstream location 58. This difference in fluid pressure reflects that the fluid flow has lost energy between location 54 and location 58 due to frictional interactions with the surfaces of first flow passage 44, particularly flow restricting element 50. These losses can be empirically correlated to a volume flowrate of a given fluid through the first flow passage 44 at a selected temperature. A variety of sensors for obtaining such information are known; in a preferred embodiment, however, a capacitive pressure sensor is used.

EXAMPLE I

Flow Measurement

Figure 16:
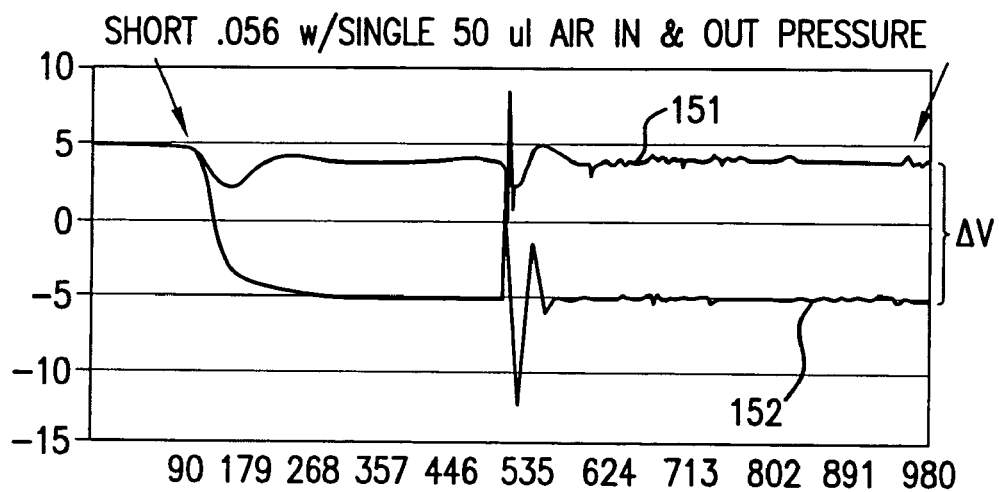
FIG. 16 is a diagram depicting flow measurement data obtained using a device in accordance with the present invention.

As embodied herein, each capacitive pressure sensor 52, 56 is used to measure pressure by detecting the change in capacitance of the pressure sensor. This measurement is accomplished by applying a voltage across each pressure sensor 52, 56. A voltage signal is then generated that is indicative of the capacitance of the pressure sensor, and therefore indicative of the pressure in the flow at either upstream location 54 or downstream location 58 at a particular point in time. Signals obtained from each pressure sensor 52, 56 are routed to processor 110. FIG. 16 depicts signal levels over time from each pressure sensor. The upstream pressure sensor output is indicated by 151 and the downstream pressure sensor output is indicated by 152. As shown, the signal levels indicated by 151 and 152 are separated by a voltage level difference. The signal level difference, indicated by $\Delta V$, is indicative of the pressure drop, and thus flowrate, between upstream location 54 and downstream location 58.

Since the relative voltage obtained from each of the pressure sensors 52, 56 is indicative of a differential pressure, it is possible to empirically establish the flowrate of fluid by a given difference in voltage output between pressure sensor 52 and pressure sensor 56. Moreover, if the Reynold's number of the flow is known for the empirical case, or if the viscosity, density and/or temperature are known of the fluid, then additional flow characteristics can be determined or calculated using known techniques. Thus, based on empirical experimentation and information, desired flow characteristics of fluid through the first fluid flow passage can be determined based on received voltage signals from the pressure sensors, as well as from the physical properties of the fluid that are known or can be closely estimated.

In accordance with a further aspect of the invention, the determining step can include determining the pressure difference between the upstream and downstream fluid pressure sensors. The determining step can further include calculating or otherwise determining a flow rate of fluid through the first fluid flow passage based on the pressure difference rather than the signal measurements.

The method of the invention further includes the step of determining the actual pressure difference between the upstream pressure sensor 52 and the downstream pressure sensor 56 instead of empirically correlating the output signal levels directly with flowrate. Flow passes through first flow passage 44 of sensor assembly 40 by passing inlet 46, upstream location 54, flow restricting element 50, downstream location 58 and outlet 48 as seen in FIGS. 9–10. Although it is not actually necessary to convert the signal output to a pressure reading before determining a flowrate through first fluid flow passage 44 of sensor assembly 40, circumstances can arise that make obtaining an actual pressure measurement desirable. For example, knowing the total pressure at the location 54 of the upstream pressure sensor 52, or at the location 58 of the downstream pressure sensor 56, or the differential pressure across flow restricting device 50 can be useful if the system is being operated at a condition that requires monitoring. Rates of fluid flow through first flow passage 44 can then be calculated based on the calculated pressure difference measured by upstream pressure sensor 52 and downstream pressure sensor 56.

EXAMPLE II

Air Detection

In accordance with another aspect of the invention, the determining step includes detecting the presence of air in the first fluid flow passage. The step of detecting air in the first fluid flow passage can include identifying convergence of the signal received from the upstream fluid pressure sensor and the signal received from the downstream fluid pressure sensor.

As embodied herein, the step of determining the presence of air in the first fluid flow passage 44 includes determining when the pressure difference measured by pressure sensors 52, 56 approaches zero.

Figure 17:
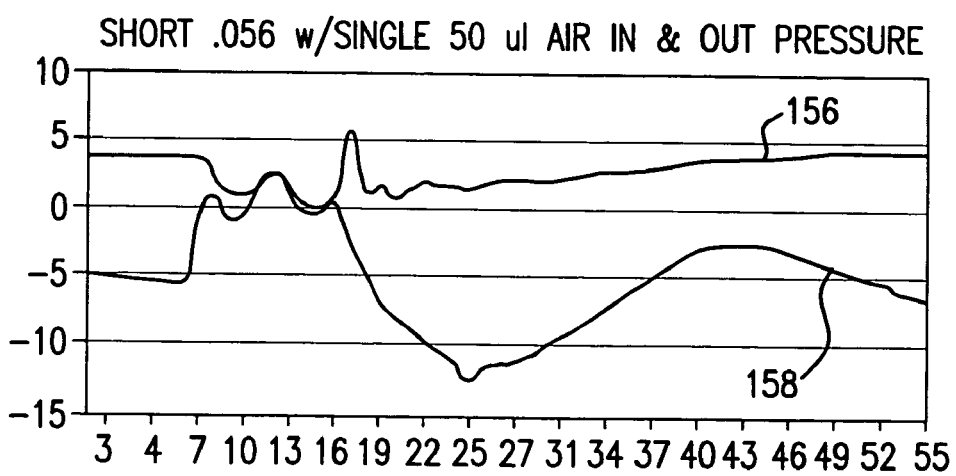
FIG. 17 is a diagram depicting air detection data obtained using a device in accordance with the present invention.

FIGS. 16–17 depict a signal output for each pressure sensor 52, 56 when a 50 microliter bolus of air is being detected in first flow passage 44. The first signal trace 151 (in FIG. 16) and 156 (in FIG. 17) which is an expanded time scale of the same data is identified as above 0 units, and the second signal trace 158 is below zero units, wherein each unit can be a measure of voltage or of relative pressure. During a normal liquid flow, the signal levels are several units apart as described above. However, when air is injected into the line, the voltage signals converge toward each other reflecting a drop in pressure differential and the presence of air in the flow line. The signal paths converge because the presence of a gas entrained in the liquid has a large difference in fluidic resistivity that causes the pressure to equalize while the air traverses the restriction rapidly and initiates a pressure shock wave in the downstream location 58 of the first flow passage 44.

For example, as a volume of air (i.e., a bubble) passes through the sensor assembly, the bubble envelopes both the upstream and downstream pressure sensors causing the pressure difference to approach zero. The volume of the sensor assembly can be small, such that very small bubbles (about 1 microliter) can be detected. As air passes over the sensors, the rapid change in fluidic resistance also generates substantial transient spikes. By monitoring these transients, a bubble can be distinguished from an upstream occlusion. In a preferred embodiment, the upstream pressure sensor 52 and downstream pressure sensor 56 are capacitance-type pressure sensors disclosed, for example, in U.S. Pat. No. 6,445,053 titled "Micro-Machined Absolute Pressure Sensor" that can be positioned less than 1 mm apart. This embodiment of a small, dual sensor assembly allows the detection and measurement of bubbles as small as 1 μl. Previous fluid flow measurement systems detected bubbles on the order of 50 μl, but could not accurately measure the size of the bubbles. In a preferred embodiment of the present invention, bubbles may be detected that are 1 μl and larger. Generally, the system would detect bubbles in the range of 1–50 μl. Larger bubbles would be detectable, but are limited merely by the time measurement of the system.

The extent of convergence of the signals is generally indicative of the amount of air detected in the flow passage. That is, the pressure differential will drop to zero when the passage is essentially filled with air. In a sensor assembly having a small volume, bubbles pass through the assembly rapidly. As a bubble passes out of the sensor assembly, the upstream pressure, P1, is restored to its initial flow value. By measuring the time the bubble traverses the device, Δt, as shown in FIG. 21, the size of the bubble can be determined. The bubble volume can be calculated according to the following formula:

Bubble volume=velocity of the bubble×Δt×cross sectional area of the flow path

For example, it is possible to quantify the actual volume of air when the system includes an upstream pump that is controlling the actual flow of fluid.

EXAMPLE III

Pulsed Flow

In accordance with yet another aspect of the invention, a method is provided further including the steps of intermittently pulsing the fluid through the first fluid flow passage and detecting the fluid pressure in the first fluid flow passage using the upstream fluid pressure sensor and the downstream fluid pressure sensor to determine the amount of fluid delivered each time the pump is pulsed. This method of obtaining flow characteristics is particularly useful when the flow rate through the fluid flow system is sufficiently low, such that background noise will interfere with signal measurements of a continuous flow.

In accordance with this aspect of the invention, a data signal output (not shown) similar to that in FIG. 16 occurs, except that it indicates pulsed operation evidenced by each signal trace gaining amplitude, dropping to zero, and then repeating transient as expected with periodic flow. The area under the signal curve can be integrated and empirically correlated to a set volume of fluid flowed through first fluid flow passage over a selected period of time. This is advantageous if it is desired to deliver extremely low dosages of a beneficial agent to a patient over an extended period of time, since a lower, steady flow over that time would not create a differential pressure signal that is sufficiently high to detect.

Specifically, when implementing a method in accordance with this aspect of the invention, it is useful to enable the flow sensing and integrating functions to only receive and compile signals received from pressure sensors 52, 56 during short bursts of fluid flow and any associated transients. Varying the average flow over a large range of delivery rates by varying the time period between the short bursts of fluid flow can assist in calibration of the system, and ensure accurate operation.

In accordance with still another aspect of the invention, a method is provided wherein the housing provided by the housing step includes a second fluid flow passage and a valve for selection of flow through the second fluid flow passage. The valve has a first condition to allow flow through the second flow passage and a second condition to prevent flow through the second flow passage. The method further includes the step of opening the valve to increase flow through the housing.

As described above, and for purpose of illustration only, housing 10 can be provided with a second fluid flow passage 80. When flow sensor device 100 is placed in locking assembly 120 in the second locked condition, protrusion 139 causes second fluid flow passage to close, as depicted in FIG. 15(c). By opening valve 140, such as by opening cover member, it is possible to increase flow through housing 10 to prime the third flow system and purge all air, or in case of a patient emergency, or other circumstance warranting a rapid increase in flowrate.

EXAMPLE IV

Occlusion Detection

Figure 18:
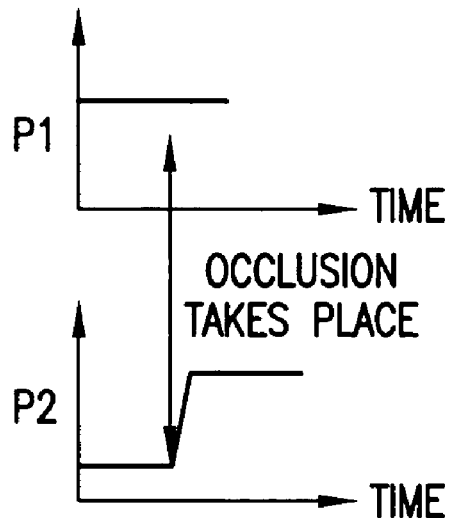
FIG. 18 is a diagram depicting pressure sensor data for a downstream occlusion in a fluid line using a device in accordance with the present invention.
Figure 19:
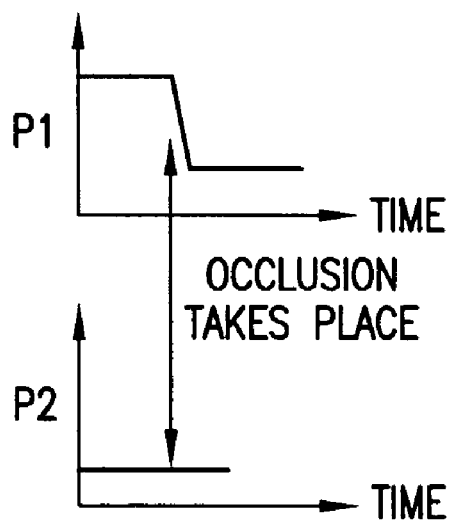
FIG. 19 is a diagram depicting pressure sensor data for an upstream occlusion in a fluid line using a device in accordance with the present invention.
Figure 20:
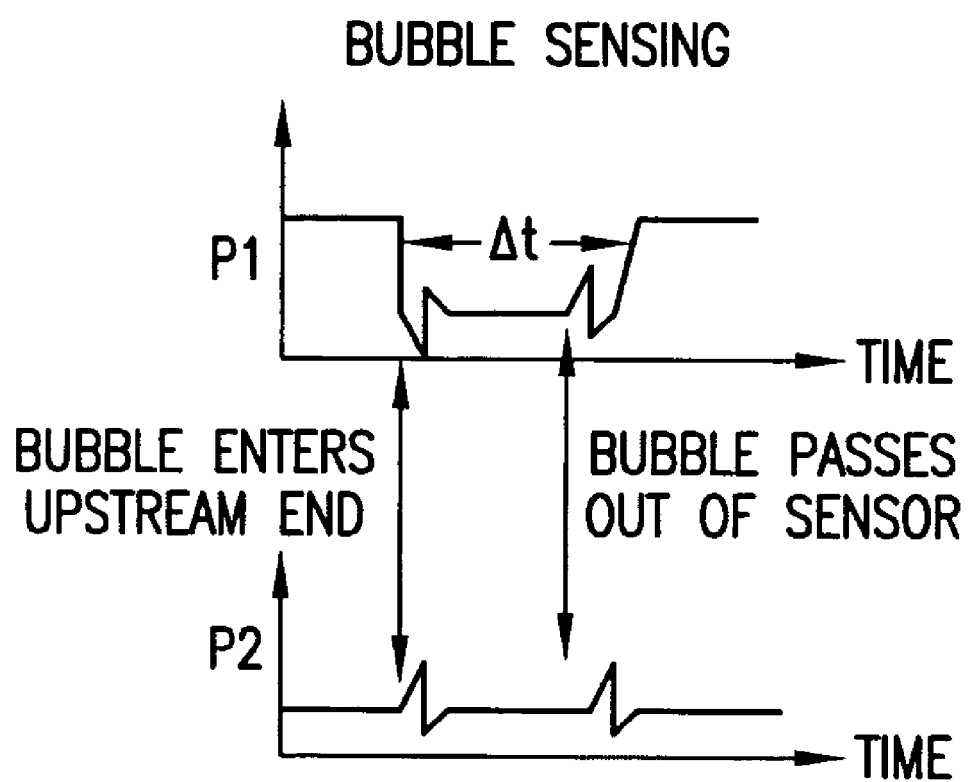
FIG. 20 is a diagram depicting pressure sensor data for a bubble traversing a device in accordance with the present invention.

In accordance with yet another aspect of the invention, the sensor assembly can be used to determine if there are occlusions, including partial occlusions, in a fluid line, and the location of the occlusions. As shown in FIG. 18, an upstream occlusion in a fluid line can be detected when the upstream pressure sensor detects a reduction in pressure while the downstream pressure sensor detects a relatively steady pressure. As shown in FIG. 19, a downstream occlusion in a fluid line can be detected when the upstream pressure sensor detects a relatively steady pressure and the downstream pressure sensor detects an increase in the downstream pressure.

It will be apparent to those skilled in the art that various modifications and variations can be made in the device, method and system of the present invention without departing from the spirit or scope of the invention. Thus, it is intended that the present invention include modifications and variations that are within the scope of the appended claims and their equivalents.

What is claimed is:

1. A variable rate infusion device, comprising:
    a fluid flow line in communication with a fluid source including a flow control means and a reservoir;
    a variable flow restriction device coupled to the fluid flow line and including a first fluid passage with a flow restricting element therealong, a second fluid passage fluidly in parallel with the first fluid passage, and a valve formed of a compressible wall member surrounding and defining a portion of the second fluid passage for selectively adjusting the second fluid passage to vary fluid flow through the variable flow restriction devices,
    wherein the compressible wall member is formed from an elastomeric material; and further comprising a housing containing the second fluid passage and a flow sensor assembly that defines the first fluid passage and the flow restricting element.

2. A variable rate infusion device according to claim 1, wherein the flow control means is a positive displacement pump.

3. A variable rate infusion device according to claim 1, wherein the flow control means is a control valve in series with the fluid flow line so as to control fluid fed by gravity.

* * * * *